United States Patent [19]

Keana

[11] Patent Number: 5,135,737
[45] Date of Patent: Aug. 4, 1992

[54] AMPLIFIER MOLECULES FOR ENHANCEMENT OF DIAGNOSIS AND THERAPY

[75] Inventor: John F. W. Keana, Eugene, Oreg.

[73] Assignee: The State of Oregon Acting by and through the State Board of Higher Education on behalf of the University of Oregon, Eugene, Oreg.

[21] Appl. No.: 403,595

[22] Filed: Sep. 5, 1989

Related U.S. Application Data

[63] Continuation-in-part of Ser. No. 928,943, Nov. 10, 1986, Pat. No. 4,863,717.

[51] Int. Cl.$^5$ .................... C12N 9/96; C07C 69/80; C07D 209/48; C07D 207/38
[52] U.S. Cl. ........................................ 424/9; 424/450; 530/383; 528/422; 548/101; 548/524; 548/486; 560/39; 560/42; 560/171; 560/164; 564/27; 564/165; 556/45; 556/110; 556/138
[58] Field of Search ............ 424/9; 548/477, 529, 548/101; 560/37, 42; 564/27, 164, 165; 562/442, 426; 558/17, 11, 14; 530/391; 528/422; 556/45, 110, 138

[56] References Cited

U.S. PATENT DOCUMENTS 4,099,918  7/1978  Keana ................................ 548/542
4,997,913  3/1991  Hellstrom et al. .................. 424/9

FOREIGN PATENT DOCUMENTS 2137612A  10/1984  United Kingdom.

OTHER PUBLICATIONS

Reddy et al Chemical Abstracts vol. 106, 1987, Abstract 33439k.
Morrison and Boyd, Organic Chemistry [Boston, Allyn and Bacon, 1979] pp. 876-880.
Borman, S., "Bioconjugate Chemistry Attracts Growing Interest," *Chem. and Eng. News,* May 8, 1989, p. 25.
Curtet, C. et al., "Selective Modification of NMR Relaxation Time in Human Colorectal Carcinoma by Using Gadolinium-Diethylenetriaminepentaacetic Acid Conjugated with Monoclonal Antibody 19-9," *Proc. Natl. Acad. Sci. USA* 83:4277 (1986).
Ehman, R. L. et al., "Enhanced MRI of Tumors Utilizing a New Nitroxyl Spin Label Contrast Agent," *Mag. Res. Imaging* 3:89 (1985).
Keana, J. F. W. and Prabhu, V. S., "trans-2,5-Dimethyl-2,5-bis(3-aminopropyl)-pyrrolidinyl-1-oxy: A trans-Diamino Azethoxyl Nitroxide," *J. Org. Chem.* 51:4300 (1986).
Keana, J. F. W. and Ogan, M. D., "Functionalized Keggin-and Dawson-Type Cyclopentadienyltitanium Heteropolytungstate Anions: Small, Individually Distinguishable Labels for Conventional Transmission Electron Microscopy. 1. Synthesis," *J. Am. Chem. Soc.* 108:7951 (1986).
Keana, J. F. W. et al., "Functionalized Keggin-and Dawson-Type Cyclopentadienyltitanium Heteropolytungstate Anions: Small, Individually Distinguishable Labels for Conventional Transmission Electron Microscopy. 2. Reactions," *J. Am. Chem. Soc.* 108:7957 (1986).
Keana, J. F. W. et al., "Synthesis of Spiro Heterocyclic Nitroxides Derived From 4-Piperidone," *J. Org. Chem.* 53:2365 (1988a).
Keana, J. F. W. et al., "Synthesis and Chemistry of N-Oxygenated Pyrroles: Crystal and Molecular Structure of a Highly Stable N-Hydroxypyrrole 18-Crown Ether Hydrate," *J. Org. Chem.* 53:2268 (1988b).
Keana J. F. W. and Pou, S., "Synthesis and Properties of Some Nitroxide α-Carboxylate Salts," *J. Org. Chem.* 54:2417 (1989).
Newkome, G. R. et al., "Cascade Molecules: Synthesis and Characterization of a Benzene[9]$^3$-Arborol," *J. Am. Chem. Soc.* 108:849 (1986).
Swyers, J., "Monoclonal Antibodies Have Diagnostic, Therapeutic Potential," *Res. Resources Reporter,* U.S. Dept. of Health & Human Services, vol. XIII, No. 4, pp. 7-9 (Apr. 1989).
Unger, E. C. et al., "Magnetic Resonance Imaging Using Gadolinium labeled Monoclonal Antibody," *Investig. Radiol.* 20:693 (1985).
Wesbey, G. E. et al., "Paramagnetic Pharmaceuticals for Magnetic Resonance Imaging," *Physiol. Chem. & Phys. & Med. NMR* 16:145 (1984).

(List continued on next page.)

Primary Examiner—Robert T. Bond
Assistant Examiner—E. C. Ward
Attorney, Agent, or Firm—Klarquist, Sparkman, Campbell, Leigh & Whinston

[57] ABSTRACT

Disclosed are amplifier molecules: various organic compounds having branched structures terminating with amine groups to which pharmacologically active groups can be chemically attached. A number of MRI contrast-enhancing agents were synthesized, each comprising plural active groups, such as stable nitroxides and complexes of trivalent metal cations. Such syntheses were successfully performed using a number of amplifiers having different branched structures, demonstrating the general utility of the pertinent chemistry in the synthesis of amplifiers having any of a wide variety of pharmacologically active groups. Amplifiers were also synthesized having linkers terminating with chemically reactive groups such as isothiocyanates, which render the amplifier bifunctional: attachable to polymers, biomacromolecules, or other biocompatible entity possessing multiple reactive sites such as terminal amines. Via such chemistry, the amplifiers are attachable to monoclonal antibodies for concentration of pharmacologically active groups at a desired site in the body.

16 Claims, No Drawings

Westerberg, D. A. et al., "Synthesis of Novel Bifunctional Chelators and Their Use in Preparing Monoclonal Antibody Conjugates for Tumor Targeting," *J. Med. Chem.* 32:236 (1989).

Koppel, Gary A., "Recent Advances with Monoclonal Antibody Drug Targeting for the Treatment of Human Cancer", *Biconjugate Chem.*, 1:13–23 (1990).

Lauffer, Randall B., "Paramagnetic Metal Complexes as Water Proton Relaxation Agents for NMR Imaging: Theory and Design", *Chem. Rev.*, 87:901–927 (1987).

Solomons, T. W., "Conjugated Unsaturated Systems", *Organic Chemistry*, pp. 470–474 (1988).

Kozak, Robert W. et al., "Radionuclide-conjugated monoclonal antibodies: a synmthesis of immunology, inorganic chemistry and nuclear science", *Tibtech*, pp. 259–264 (Oct. 1986).

Keana, John F. W. et al., "Nitroxides as Potential Contrast Enhancing Agents for MRI Application: Influence of Structure on the Rate of Reduction by Rat Hepatocytes, Whole Liver Homogenate, Subcellular Fractions, and Ascorbate", *Magnetic Resonance in Medicine,* 5:525–536 (1987).

Keana, J. F. W., "Synthesis and Chemistry of Nitroxide Spin Labels," *Spin Labeling in Pharmacology*, Chapter 1 (1984).

AMPLIFIER MOLECULES FOR ENHANCEMENT OF DIAGNOSIS AND THERAPY

CROSS REFERENCE TO RELATED APPLICATION

This application is a continuation-in-part of co-pending U.S. patent application Ser. No. 06/928,943 filed Nov. 10, 1986, now U.S. Pat. No. 4,863,717 incorporated herein by reference.

FIELD OF THE INVENTION

This invention relates to organic compounds for diagnosis and therapy, the compounds having a multiplicity of functional groups for enhanced or prolonged effect and the compounds including target-specific agents.

BACKGROUND OF THE INVENTION

A number of medical procedures pertaining to diagnosis and therapy require the administration to the patient of special chemicals in order to enhance the quality or degree of the anticipated result of the procedure. Representative examples of general classes of such chemicals include contrast-enhancing agents for Magnetic Resonance Imaging (MRI), fluor-tagged agents for fluorescent labeling of specific cells or organs, electron-dense agents for x-ray procedures, and radionuclide-labeled agents used to deliver radioactive isotopes to particular deep-seated tumors, and drug-labeled agents used to deliver multiple drug therapeutic molecules to the target site. Compounds administered for such purposes comprise molecules generally having one or more distinctive chemical groups or functional moieties attached thereto that give the molecule its desired pharmacologic utility.

As used herein, a pharmacologically active group or molecule is a group or molecule, respectively, having a chemical structure providing a desired diagnostic or therapeutic effect in the body of a human or other warm-blooded animal. For example, stable organic nitroxides are pharmacologically active because they serve as spin relaxers useful for contrast enhancement in the MRI diagnostic technique.

Many of the chemical compounds currently used as pharmacologic agents are toxic to the patient, especially in high dosages. In many cases, optimal results can only be obtained when the patient receives more of the agent than can be physiologically tolerated. In other words, the therapist is often faced with treading the fine line between obtaining the best possible pharmacologic result and either seriously intoxicating or killing the patient.

Other such compounds in current use, such as certain MRI contrast-enhancing agents, are so short-lived in a physiological environment that massive dosages need to be administered to obtain even a slight effect. For example, stable nitroxide free radicals are rapidly reduced when injected into the body. Nitroxide free radicals are metabolically converted in vivo to diamagnetic forms with consequent loss of their ability to provide contrast for MRI. In the past, "reduction" problems have been handled by injecting large amounts of simple nitroxide compounds, such as those containing a single nitroxide radical, into the patient with the intent of "swamping" the reduction reaction. Unfortunately, such large dosages of nitroxides are both toxic and cause osmotic disequilibria in the body.

In other instances, large dosages of pharmacologic chemicals are necessary because there are few practical ways to direct a particular compound to the desired target in the body where the compound can be concentrated for optimal effect. Without some way to render the compound "targeting," it is rapidly diluted in body circulatory liquid. To counteract this problem, massive dosages are sometimes administered in order to obtain a minimal concentration at the site of interest. Unfortunately, such large dosages can be toxic to the patient or otherwise cause serious physiochemical imbalances.

One way to concentrate diagnostic or therapeutic molecules at a given locus in the body is to attach the molecules to antibodies specific for (i.e., seroreactive with) the target cells of interest. To effect such attachment of a molecule, a bifunctional form thereof is first synthesized, comprising the pharmacologically active group on one end of the molecule, a protein-reactive-group on the other end, and a linker group serving as a structural bridge joining the ends of the molecule together. The protein-reactive group on the bifunctional molecule reacts with one or more specific moieties on the antibodies, yielding a population of conjugated antibodies ("decorated" or "tagged") having one or more of the desired diagnostic or therapeutic molecules chemically bonded thereto. One example of a protein-reactive group is the isothiocyanate moiety ($-N=C=S$). Isothiocyanate is reactive with the $\epsilon$-amino group of lysine, a common amino acid in proteins, yielding a thiourea ($-NHSNH-$) linkage between the lysine and the linker, and the linker terminating with the pharmacologically active group. When the conjugated antibodies are administered to a patient, they carry the attached diagnostic or therapeutic agent to the target cells to which the antibodies become attached.

Although the conjugated antibody concept has been successful in some instances, it has several drawbacks when utilized with many existing pharmacologic agents that have only one active group per molecule. First, as reviewed above, some such agents, such as nitroxides for MRI, are short-lived in the body. Merely conjugating them to target-specific antibodies would help concentrate them at the desired target, but would not slow the rate at which the nitroxides are reduced in vivo. Attaching larger numbers of bifunctional nitroxides to the antibodies would seem to increase both the effective concentration of active nitroxide at the target and the time before the effective concentration drops below the minimal required level. Unfortunately, however, attaching too many conjugates to an antibody may destroy the antibody's immunological activity, i.e., its ability to attach to the target. If it were possible to attach fewer nitroxide conjugates to the antibody, where each conjugate has more than the single nitroxide group found in existing MRI contrast-enhancing agents, one would obtain antibodies that retain their ability to bind to the target while having a sufficient number of attached nitroxides to achieve the desired contrast of the target in a magnetic resonance image.

Therefore, the stated drawbacks of many existing diagnostic and therapeutic agents are due to their having only one or a very few diagnostically or therapeutically active groups per molecule, respectively. If one could "amplify," or increase, the number of such active groups per molecule, it would be possible to achieve enhancement of the intended medical result with less morbidity to the patient.

In my co-pending U.S. patent application, Ser. No. 06/928,943, now U.S. Pat. No. 4,863,717 of which the present application is a continuation-in-part, several novel techniques for providing long-lasting nitroxide-bearing MRI contrast agents were disclosed. The first technique involved the construction of liposomes, the lipid bilayers of which incorporated numerous long-chain nitroxides in the form of fatty esters. The nitroxides were exposed on the exterior of each liposome and an oxidant was encapsulated inside the liposome. Reduced nitroxides flipped to the inside of the liposome, became re-oxidized, then returned to the outside of the liposome. Because the nitroxides are thus "regenerated," the MRI contrast-enhancing effect imparted by a dose of such liposomes administered to a patient is long-lasting. Consequently, lower dosages are required to achieve a desired image contrast for a longer period of time than with previous nitroxide-based MRI contrast agents.

The second technique disclosed in my co-pending application involved the synthesis of molecules patterned after the radially symmetrical, branched molecules, termed arborols. The branches of the new molecules terminated with nitroxide groups. Such molecules can be administered to the patient in relatively low dosages for reduced toxicity and reduced osmotic disequilibria while still supplying high effective numbers of nitroxide groups for adequate MRI contrast enhancement during the time required for obtaining an MRI image.

There remains, however, a need for other diagnostic and therapeutic agents comprising molecules with multiple numbers of pharmacologically active groups, respectively, including agents that can be readily made bifunctional to become attachable either to specific biomolecules such as antibodies or to other loci within the body without the need to administer prohibitively large doses of the agents to the patient

SUMMARY OF THE INVENTION

The present invention comprises a number of amplifier molecules: branched organic molecules having a multiplicity of terminal amines to which chemical groups having particular pharmacologic utility can be chemically attached. Additionally, each amplifier molecule may contain a unique, chemically reactive group which is used to attach the assembly to the target. The present invention also includes a number of such branched pharmacologic molecules synthesizable from the amplifier molecules.

One class of amplified compounds comprising the present invention includes MRI contrast-enhancing agents having two or more stable nitroxides per molecule. Another class of amplified compounds for MRI includes agents having two or more gadolinium-complexing groups per molecule. Using similar chemistry, a number of different chemical groups conferring other enhanced diagnostic or therapeutic utility to amplifier molecules can be attached to the terminal amines of the amplifier molecules. Such groups include chemotherapeutic agents for treating cancers and other diseases, toxins, electron-dense moieties for x-ray, radionuclides and fluorophores.

In addition, "linkers" terminating with chemically reactive groups can be attached to the amplifier molecules of the present invention. For example, the amplifiers may have a linker terminating with an isothiocyanate moiety, enabling the molecule to be attached to biological macromolecules such as proteins, including immunoglobulins (antibodies). Attaching the compound to a monoclonal antibody seroreactive with a desired physiological or anatomical site renders the compound site-specific or "targeted," enabling the compound to be selectively enriched at a desired site in the body for even greater effect.

Amplified compounds have particular pharmacologic utility when the physician wishes to achieve the greatest possible diagnostic or therapeutic effect with a particular agent at the lowest possible dose, thereby reducing morbidity, mortality risk, disequilibria, and other undesirable concentration-related side effects.

Accordingly, one object of the present invention is to provide various branched organic molecules, at least some of the branches of which terminating with amines to which other chemical groups having pharmacologic utility can be chemically attached, thereby yielding molecules having an enhanced, or "amplified," effect per mole compared with existing pharmacologic agents.

Another object is to provide such compounds, the molecules of which having a linker portion terminating with a reactive moiety useful for attaching the molecule to target-specific biomolecules.

Another object is to provide such compounds already chemically linked to target-specific biomolecules such as monoclonal antibodies for selective concentration of the compound at the physiological or anatomical site of interest.

Another object is to provide such compounds having a plurality of stable nitroxides per molecule for enhanced contrast of body structures for Magnetic Resonance Imaging (MRI).

Another object is to provide such compounds having a plurality of gadolinium-complexing groups per molecule for enhanced contrast of body structures for MRI.

These and other objects and advantages of the invention will be apparent from the following detailed description.

DETAILED DESCRIPTION

As used herein, an "amplifier" or "amplifier molecule" is a chemical compound having a multiplicity of terminal amine moieties, each serving as a locus to which one or two of any of several desired functional groups can be chemically attached, thereby allowing the synthesis of branched molecules having a multiplicity of functional groups per molecule. As described herein, chemical groups having pharmacologic utility can be attached to the terminal amines of amplifier molecules, yielding molecules having an enhanced effect over molecules having only one such group.

An "amplification factor" refers to the number of terminal amines present in each amplifier molecule. For example, a molecule with an amplification factor of six has six terminal amines. Each terminal amine, in turn, can accept either one or two functional groups, depending on the particular group added thereto, in place of the hydrogen atoms.

Any of the amplified pharmacological compounds of the present invention may be introduced into the body of a human or other warm-blooded animal by any pharmacologically suitable carrier. Generally, buffered isotonic saline solution is the carrier of choice. Compounds intended for diagnostic use are generally administered intravenously such as presently done, for example, with gadolinium-DTPA for MRI contrast enhancement.

The following basic methods and equipment were used during the work resulting in the present invention:

Melting points were obtained on a Thomas Hoover apparatus and were uncorrected. NMR spectra were recorded on a Nicolet QE 300 spectrometer in CDCl$_3$ unless otherwise stated. Chemical shifts are expressed in d units relative to tetramethylsilane (Me$_4$Si). IR spectra were recorded on a Nicolet DX-FT IR spectrometer in CDCl$_3$ solvent unless otherwise stated. Elemental analyses were determined by Desert Analytics, Tucson, Ariz. All reactions were routinely run under N$_2$ atmosphere. For flash chromatography, Grade 633, 200-425 mesh 60 Å silica gel (Aldrich) was used. Solvents were routinely distilled.

A. Synthesis of an Amplifier Molecule Derived from 3,5-Bis(bromomethyl)benzoic Acid Having an Amplification Factor of Two The starting compound, 3,5-bis(azidomethyl)benzoic acid, was as described in Young and Chang, *J. Am. Chem. Soc.*:107:898 (1985). To a solution of 3,5-bis(bromomethyl)benzoic acid (compound 1) (0.815 g, 2.64 mmol) in 25 mL acetone was added a solution of sodium azide (0.715 g, 11.0 mmol) in 2.5 mL water. The solution was refluxed for 1 h and concentrated in vacuo. The concentrate was acidified with 2N HCl and extracted with ether. The extract was washed with brine, dried (MgSO$_4$), and concentrated to dryness giving 3,5-bis-(azidomethyl)benzoic acid (compound 2) (610 mg, 99% yield) as a colorless oil: IR (film) 3100-2900, 2105, 1698, 1608 cm$^{-1}$; NMR δ 4.48 (s, 4), 7.56 (s, 1), 8.05 (s, 2).

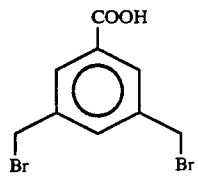

(1)

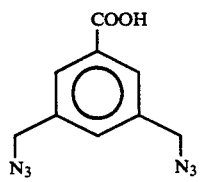

(2)

Triphenylphosphine (1.31 g, 5.0 mmol) was added to a stirred solution of compound 2 (464 mg, 2.00 mmol) in 10 mL dry tetrahydrofuran (THF) at 25° C. The solution became warm and turned yellow as N$_2$ was given off. A yellow gum separated which was collected. The gum was dissolved in 20 mL of 20% HCl, refluxed for 1 h, and then allowed to stand at 25° C. overnight. The solvent was removed and the residue dissolved in 25 mL water, extracted with ether, and then with chloroform (CHCl$_3$). The aqueous phase was evaporated to dryness and the crystalline residue was recrystallized from MeOH-ether to give 3,5-bis(aminomethyl)benzoic acid hydrochloride (compound 3) (355 mg, 70% yield) as a white powder: mp 285°-287° C.; IR (nujol) 3500-2500, 1711, 1614, 1597, 1511, 1482, 1190, 1124 cm$^{-1}$; NMR (D$_2$O) δ 4.30 (s, 4), 7.75 (s, 1), 8.12 (s, 2). Analysis calculated for C$_9$H$_{14}$Cl$_2$N$_2$O$_2$: C, 42.71; H, 5.57; N, 11.07; found: C, 42.35; H, 5.54; N, 10.89. Compound 3 is a novel amplifier molecule having an amplification factor of two.

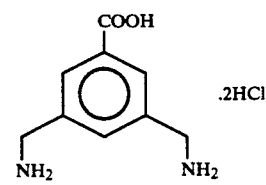

(3)

B. Synthesis of an Amplifier Molecule Derived from Methyl 3,5-Bis(bromomethyl)benzoate Having an Amplification Factor of Two A compound similar to compound 3 having an amplification factor of two may be synthesized by either of two methods that differ from each other in the method employed to synthesize the intermediate compound in the synthetic pathway. In both methods, methyl 3,5-bis(bromomethyl)benzoate (compound 4), Staab and Kirrstetler, *Liebig's Ann. Chem.* p. 886 (1979), is used as the starting compound.

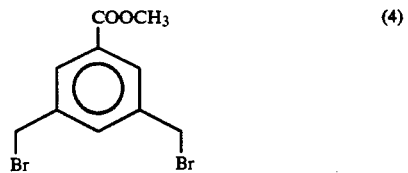

(4)

In the first method, a solution of sodium azide (524 mg, 8.00 mmol) in 5 mL water was added to a solution of methyl 3,5-bis(bromomethyl)benzoate (compound 4) (644 mg, 2.00 mmol) in 50 mL acetone. The solution was refluxed for 1 h and then concentrated. The residue was extracted with ether. The extract was washed with water, then with brine, then dried (MgSO$_4$). Evaporation gave the intermediate compound methyl 3,5-bis-(azidomethyl)benzoate (compound 5) (431 mg, 75% yield) as a colorless oil: IR (film) 2106, 1724, 1610, 1435 cm$^{-1}$; NMR δ 3.95 (s, 3), 4.44 (s, 4), 7.49 (s, 1), 7.97 (s, 2).

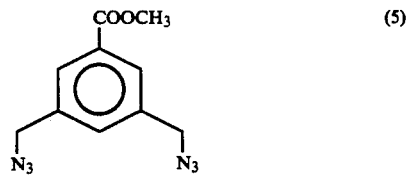

(5)

Intermediate compound 5 can also be synthesized by the following method, according to Koziara et al., *Synthesis*, p. 202 (1985): To a stirred solution of methyl 3,5-bis(bromomethyl)benzoate (compound 4) (322 mg, 1.00 mmol) in 2 mL benzene was added sodium azide (262 mg, 4.00 mmol) and tetrabutylammonium bromide (64 mg, 0.20 mmol). The solution was refluxed for 6 h and then allowed to cool to 25° C. Ether was added and the organic phase was washed with water, then with brine, and then dried (MgSO$_4$). Concentration to dryness gave a colorless oil that was chromatographed over silica gel. Elution with 10:1 hexane:ethyl acetate gave the pure intermediate, methyl 3,5-bis(azidomethyl)benzoate (compound 5) (210 mg, 85% yield) as a colorless oil.

Triphenylphosphine (944 mg, 3.60 mmol) was added to a stirred solution of the intermediate compound 5

(369 mg, 1.50 mmol) in 5 mL dry THF. After 2 hr at 25° C., water (90 mg, 5.0 mmol) was added and the mixture was allowed to stir overnight. Then, 15 mL of 2N HCl was added and the mixture extracted with ether. The extract was concentrated to dryness and the residue crystallized from MeOH-ether to give methyl 3,5-bis-(aminomethyl)benzoate hydrochloride (compound 6) (328 mg, 61% yield) as a white powder: mp 262°-264° C.; IR (nujol) 3200–2600; 1713, 1614 cm ; NMR (D$_2$O) δ 3.97 (s, 3), 4.30 (s, 4), 7.76 (s, 1), 8.15 (s, 2). Analysis calculated for C$_{10}$H$_{16}$Cl$_2$N$_2$O$_2$: C, 44.96, H, 6.04, N, 10.49; found: C, 44.92; H, 6.11; N, 10.34.

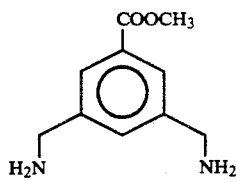
(6)

Compound 6 is also a novel amplifier molecule having an amplification factor of two. As can be seen, compound 6 is a methyl-ester form of compound 3, the ester group being an alternative to the carboxyl form 3 and being more compatible with certain other chemical reagents in terms of providing a site for additional substitutions via known chemistry. The two primary amine groups on each of diamines 3 and 6 are sites at which various pharmacologically active groups can be chemically attached via alkylation, acylation, or other addition reaction occurring at primary or secondary amines. As illustrative examples, nitroxide free radicals can be attached by a number of reactions as described below.

C. Synthesis of Amplifier Molecules Derived from Methyl 3,5-Bis(bromomethyl)benzoate Having an Amplification Factor of Six To a stirred solution of 3-bromo-2,2-bis(bromomethyl)-1-propanol (compound 7) (3.25 g, 10.0 mmol) in 60 mL dimethyl formamide (DMF) was added sodium azide (7.80 g, 120 mmol) in 6 mL water. Compound 7 is described in Dyachenko and Lukina, *Izv. Akad. Nauk. SSSR Ser. Khim.* 12:2237 (1966). The solution was heated at 100° C. for 1 d and most of the solvents were removed in vacuo. Water was added to the residue, followed by extraction with ether. The extract was washed with water, then with brine, then dried (MgSO$_4$). Evaporation gave an oil that was chromatographed over silica gel. Elution with 3:1 hexane:ethyl acetate gave 3-azido-2,2-bis(azidomethyl)-1-propanol (compound 8) (1.86 g, 88% yield) as a colorless oil: IR (film) 3430, 2136, 2090 cm$^{-1}$; NMR δ 1.72 (t, 1), 3.38 (s, 6), 3.55 (d, 2). Analysis calculated for C$_5$H$_9$N$_9$O: C, 28.44; H, 4.29; N, 59.69; found: C, 28.91; H, 4.26; N, 59.51.

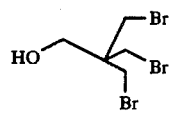
(7)

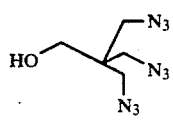
(8)

Alcohol 8 (231 mg, 1.10 mmol), tetrabutylammonium hydrogen sulfate (170 mg, 0.50 mmol), and 1 mL of 50% w/w aqueous NaOH were added to a stirred solution of methyl 3,5-bis(bromomethyl)benzoate (compound 4) (161 mg, 0.50 mmol) in 5 mL THF. After 1 h (reaction complete by TLC) the mixture was poured onto ice. The solution was acidified with 1.5 mL concentrated HCl, then extracted with ether. The extract was washed with water, then with brine, dried (MgSO$_4$), and evaporated to give an oil that was chromatographed over silica gel. Elution with 5:1 hexane:ethyl acetate gave pure (by TLC) methyl 3,5-bis[1-(3-azido-2,2-bis-(azidomethyl)propyl)oxymethyl]benzoate (compound 9) (157 mg, 54% yield) as a colorless oil: IR (film) 2104, 1724, 1608, 1451, 1306, 1102 cm$^{-1}$; NMR δ 3.34 (s, 4), 3.36 (s, 12), 3.94 (s, 3), 4.56 (s, 4), 7.46 (s, 1), 7.93 (s, 2).

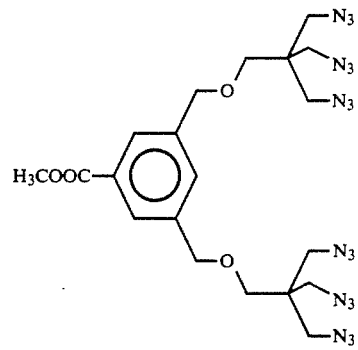
(9)

Continued elution of the column with 2:1 hexane:ethyl acetate gave pure (by NMR) 3,5-bis[1-(3-azido-2,2-bis(azidomethyl)propyl)oxymethyl]benzoic acid (compound 10) (95 mg, 33% yield) as a light yellow oil: IR (film) 3300–2800, 2108, 1694, 1608, 1451, 1305, 1105 cm$^{-1}$; NMR δ 3.36 (s, 4), 3.37 (s, 12), 4.58 (s, 4), 7.52 (s, 1), 8.01 (s, 2). Analysis calculated for C$_{19}$H$_{24}$N$_{18}$O$_4$: C, 40.14; H, 4.25; N, 44.35; found C, 40.43; H, 4.13; N, 43.61.

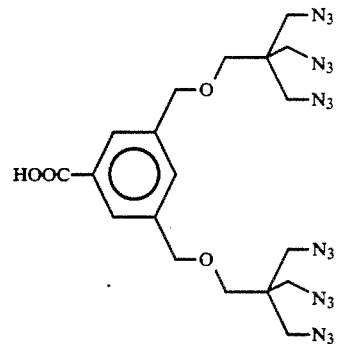
(10)

Acid 10 was also prepared by hydrolysis of ester 9 via the following method: A combined solution of ester 9 (437 mg, 0.750 mmol) in 15 mL of 1:1 THF:MeOH and 2 mL of 1N NaOH was allowed to stand at 25° C. The solution was acidified with 2N HCl, diluted with water, and extracted with ether. The extract was washed with water, then with brine, dried (MgSO$_4$), and evaporated to give pure (by NMR) acid 10 (413 mg, 97% yield) as a light yellow oil.

Acid 10 was converted into an amplifier molecule having an amplification factor of six and a diene tail (the diene tail useful for subsequent attachment of one or more reactive moieties to, for example, render the molecule bifunctional) via the following synthetic pathway: To a stirred solution of (E) 3,5-hexadien-1-ol (850mg, 8.66 mmol) (compound 11) and Et$_3$N (1.28 g, 12.6 mmol) in 7 ml of CH$_2$Cl$_2$ at 0° C. was added dropwise methanesulfonyl chloride (1.49g, 13.0 mmol). After 30 min the mixture was worked up to give 1.60 g of crude mesylate (compound 12).

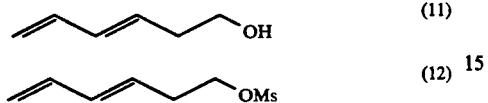

The mesylate 12 was purified by column chromatography rather than vacuum distillation, according to Keana and Ogan, J. Am. Chem. Soc. 108:7951 (1986). A solution was prepared by adding 885 mg (5.00 mmol) of mesylate 12 to 20 mL DMF and 2 mL water. Sodium azide (1.62 g, 25.0 mmol) was added to the solution. The resulting mixture was stirred at 100° C. for 2 h, cooled to 25° C., diluted with water, and extracted with ether. The extract was washed with water, then with brine, dried (MgSO$_4$), and evaporated to give (E)-hexa-3,5-dienyl azide (compound 13) (572 mg, 93% yield) as a light yellow oil: IR (film) 2100, 1654, 1604 cm$^{-1}$; NMR δ 2.39 (q, 2), 3.33 (t, 2), 5.03-5.19 (dd, 2), 5.67 (m, 1), 6.12-6.38 (m, 2). This low-boiling oil contained a trace of DMF but was sufficiently pure for the next reaction.

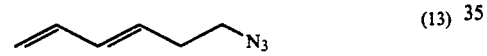

Triphenylphosphine (1.31 g, 5.00 mmol) was added to a solution of crude azide 13 (572 mg, 4.65 mmol) in 10 mL dry THF. After a 30-minute stir at 25° C., the mixture was refluxed for 30 min and then cooled. Water (180 mg, 10.0 mmol) was added and the mixture was stirred overnight, refluxed for 1 h, then cooled to 0° C. The mixture was acidified with 1N HCl and extracted with ether. The aqueous phase was basified with 1N NaOH, saturated with NaCl, and extracted with ether. The extract was dried (K$_2$CO$_3$) and evaporated to give (E)-hexa-3,5-dienylamine (compound 14) (303 mg, 62% yield based on mesylate 12) as a yellow oil: IR (film) 3500-2800, 1653, 1604 cm$^{-1}$; NMR δ 1.31 (brs, 2), 2.24 (q, 2), 2.78 (t, 2), 4.98-5.15 (dd, 2), 5.67 (m, 1), 6.08-6.39 (m, 2).

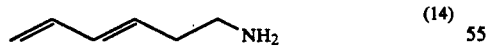

To facilitate the elemental analysis of the amine 14, it was advantageous to convert the compound to its toluenesulfonate salt. Amine 14 is too volatile for accurate analyses and also tends to undergo air oxidation.

The toluenesulfonate salt 15 of amine 14 was prepared by treating the amine 14 with a solution of p-toluenesulfonic acid in MeOH followed by chilling in a freezer. The precipitated salt was collected. The toluenesulfonate salt was found to have the following properties: mp 125°-126° C.; IR (nujol) 3079, 1624, 1602, 1525 cm$^1$; NMR (D$_2$O) δ 2.35 (s, 3), 2.41 (q, 2), 3.03 (t, 2), 5.05-5.22 (dd, 2), 5.65 (m, 1), 6.18-6.43 (m, 2), 7.48 (ABq, 4). Analysis calculated for C$_{13}$H$_{19}$NO$_3$S: C, 57.97; H, 7.11; N, 5.20; found: C, 58.03; H, 7.15; N, 5.23.

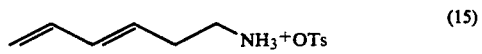

1,1-carbonyldiimidazole (19.5 mg, 0.12 mmol) was added to a stirred solution of acid 10 (56.8 mg, 0.10 mmol) in 1 mL dry THF. After 2 h a solution of amine 14 (9.7 mg, 0.10 mmol) in 0.5 mL THF was added. After a 30-minute stir, the mixture was evaporated to dryness and the residue chromatographed over silica gel. Elution with 3:1 hexane:ethyl acetate gave pure (by NMR) N-((E)-hexa-1,3-dienyl)-3,5-bis[1-(3-azido-2,2-bis-(azidomethyl)propyl)-oxymethyl]benzamide (compound 16) (48 mg, 74% yield) as a colorless oil: IR (film) 3328, 2106, 1642, 1602, 1542, 1450, 1303, 1101 cm$^{-1}$; NMR δ 2.42 (q, 2), 3.34 (s, 4), 3.35 (s, 12), 3.53 (m, 2), 4.55 (s, 4), 5.10 (m, 2), 5.70 (m, 1), 6.10-6.40 (m, 3), 7.38 (s, 1), 7.63 (s, 2). Analysis calculated for C$_{25}$H$_{33}$N$_{19}$O$_3$: C, 46.36; H, 5.14; N, 41.09; found: C, 46.39; H, 4.94; N, 40.16.

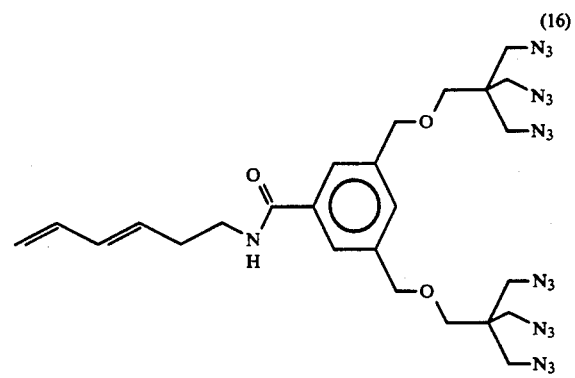

Triphenylphosphine (420 mg, 1.60 mmol) was added to a stirred solution of the hexaazide 16 (129 mg, 0.200 mmol) in 6 mL dry THF. After 2 h at 25° C., water (144 mg, 8.0 mmol) was added and the mixture was refluxed overnight. The mixture was cooled, diluted with 6 mL water, and extracted with ether. The aqueous phase was evaporated in vacuo to give pure (by NMR) N-((E)-hexa-1,3-dienyl)-3,5-bis[1-(3-amino-2,2-bis(aminomethyl)-propyl)oxymethyl] benzamide (compound 17) (85 mg, 86% yield) as a colorless sticky gum-like oil: IR (film) 3650-2800, 1642, 1601, 1455, 1330, 1102 cm$^{-1}$; NMR (D$_2$O) δ 2.37 (q, 2), 2.51 (s, 12) , 3.36 (s, 4 , 3.44 (t, 2), 4.53 (s, 4), 5.00-5.17 (dd, 2) , 5.76 m, (1), 6.11-6.40 (m, 2), 7.55 (s, 1), 7.62 (s, 2). Hexaamine 17 is a novel amplifier molecule -with an amplification factor of six. As with any of the other amplifier molecules of the present invention, various pharmacologically active groups can be attached via chemistry as herein described to the amino groups of the hexaamine 17. The diene tail can be either left unchanged or modified via, for example, a Diels-Alder addition in order to render the compound capable of bonding to a protein (see Section E, below).

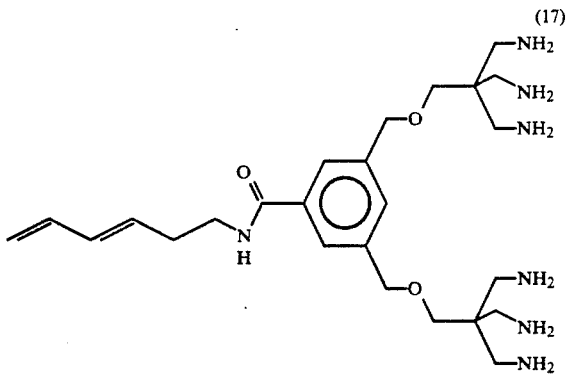

(17)

To facilitate elemental analysis of the hexaamine 17, it was converted to its toluenesulfonate salt (compound 18) via the following procedure: A 9.8-mg (0.020 mmol) sample of hexaamine 17 was dissolved in 0.7 mL EtOH and treated with a solution of p-toluenesulfonic acid (22.8 mg, 0.12 mmol) in 1.0 mL EtOH. The mixture was chilled in the freezer and the precipitated salt was collected, washed with acetone and ether, and dried, giving the salt (15.6 mg, 50% yield) as a white solid: mp 236°–238° C. (dec); IR (nujol) 3444, 3029, 1661, 1638, 1603, 1535 1177, 1128 cm$^{-1}$; NMR (D$_2$O) δ 2.28 (s, 18), 2.34 (q, 2), 3.29 (s, 12), 3.40 (t, 2), 3.76 (s, 4), 4.61 (s, 4), 5.02 (dd, 2), 5.72 (m, 1), 6.05–6.40 (m, 2), 7.38 (ABq, 24), 7.46 (s, 1), 7.63 (s, 2). Analysis calculated for C$_{67}$H$_{93}$N$_7$O$_{21}$S$_6$.2H$_2$O: C, 51.55; H, 6.26; N, 6.28: found: C, 51.54; H, 6.12; N, 6.49.

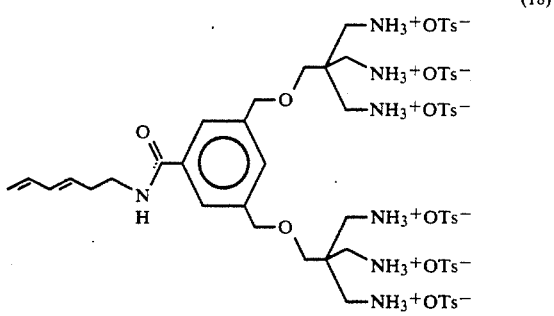

(18)

D. Conversion of Hexaamine 17 to an MRI Contrast Agent Having Twelve Stable Nitroxide Groups Hexaamine 17 is converted to a corresponding twelve-membered nitroxide form via a base-catalyzed cleavage of epoxide-tailed organic nitroxides, resulting in the addition of the nitroxides to the hexaamine. Although virtually any pharmacologically active group possessing an epoxide tail can be added to hexaamine 17 via the chemistry described below, the example described was performed with a particular pyrrolidine stable nitroxide. (As used herein, a stable nitroxide is an organic nitroxide having a pharmacologically useful shelf life after synthesis. In other words, the nitroxide has sufficient stability to participate in addition reactions as herein described without becoming reduced or otherwise chemically altered so as to lose its spin-relaxation property. What is acceptable as a shelf life will depend upon how and when the compound is to be used in a mammalian or other body of a warm-blooded animal after synthesis of the compound.)

First, 2,2,5-trimethyl-5-[(2-oxiranylmethoxy)ethyl]-tetrahydropyrrole-1-oxy (compound 20) was synthesized according to Mouzin et al., Synthesis, p. 117 (1983). To begin the synthesis of compound 20, epichlorohydrin (0.4 mL, 5.0 mmol) was added with stirring at 0° C. to oily nitroxide alcohol 19 (172 mg, 1.00 mmol). Compound 19 is described in Hideg and Lex, J. Chem. Soc. Perkin Trans. I. p. 1117 (1987). Afterward, 16 mg tetrabutylammonium hydrogen sulfate and 0.7 mL of 50% aqueous NaOH were added. The mixture was stirred at 25° C. for 3 h and then poured onto ice and extracted with ether. The extract was washed with brine, then dried (MgSO$_4$), and evaporated. The oily residue was chromatographed over silica gel. Elution with 5:4 hexane:ethyl acetate gave the pyrrolidine nitroxide epoxide 20 (211 mg, 92% yield) as a yellow oil: IR (film) 1462, 1368, 1256, 1111 cm$^{-1}$; ESR (MeOH) 3 lines, a$_n$x=15.9 G. Analysis calculated for C$_{12}$H$_{22}$NO$_3$.0.2 H$_2$O: C, 62.15; H, 9.73; N, 6.04; found: C, 62.29; H, 10.05; N, 6.30.

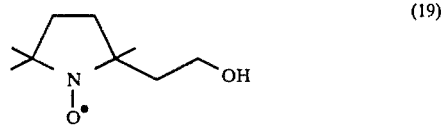

(19)

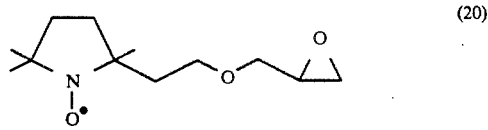

(20)

Pyrrolidine nitroxide epoxide 20 (228 mg, 1.00 mmol) was added to a solution of hexaamine 17 (24.6 mg, 0.050 mmol) in 0.5 mL EtOH. The solution was refluxed for 7 d and then concentrated to dryness. The residue was chromatographed over silica gel. Elution with 50:8:1 CHCl$_3$:MeOH:H$_2$O gave N-((E)-Hexa-1,3-dienyl)-3,5-bis{1-[3-N,N-bis[1-(2-hydroxy-4-oxa-6(2,2,5-tr imethyltetrahydropyrrol-1-oxy-5-yl))hexyl]amino-2,2-bis[N,N-bis(1-(2-hydroxy-4-oxa-6-(2,2,5-trimethyltetrahydropyrrole-1-oxy-5-yl)hexyl))-aminomethyl]-propyl]oxymethyl}benzamide (compound 21) (118 mg, 73% yield) as a sticky yellow oil: IR (film) 3367, 1652, 1605, 1540, 1463, 1368, 1119 cm$^{-1}$; ESR (MeOH) one broad line. Analysis calculated for C$_{169}$H$_{309}$N$_{19}$O$_{39}$7 H$_2$O: C, 60.46; H, 9.70; N, 7.93; found: C, 60.33; H, 9.67; N, 8.14.

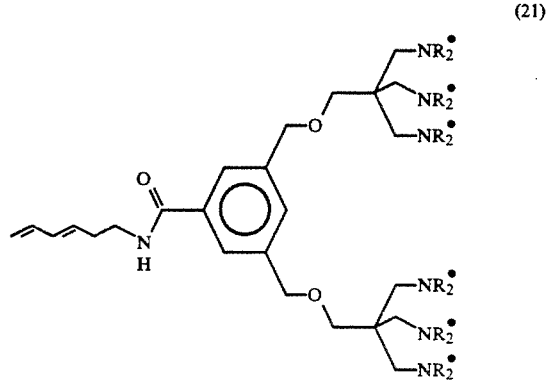

(21)

wherein R' is

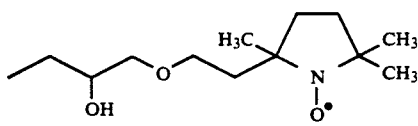

As can be seen, nitroxide diene 21 contains twelve pyrrolidine nitroxide groups and can be used as an MRI contrasting agent without attaching the molecule to any specific anatomical or macromolecular target. In similar epoxide cleavage reactions, it is possible to attach other stable nitroxides, including other pyrrolidine, piperidine, doxyl and proxyl nitroxides to the hexaamine 17. (Reference is made to Keana, U.S. Pat. No. 4,099,918, which is incorporated herein by reference.) In other words, virtually any stable nitroxide having the desired spin-relaxing utility can be attached to primary amines on an amplifier molecule such as hexaamine 17 by first converting a first end of the nitroxide to an epoxide, followed by reaction of the epoxide with an amine group on the amplifier, using chemistry similar to that described above.

Moreover, although the above synthesis was described using a pyrrolidine nitroxide example, virtually any compound having a first group possessing pharmacologic utility and a second group comprising a terminal epoxide can be attached to an amplifier molecule such as hexaamine 17 by similar chemistry. This is because epoxides quite readily undergo base-catalyzed cleavage for which primary amines serve as a useful nucleophile. The cleavage of the epoxide is predictably accompanied by linkage to the amine of the pharmacologically active group.

The nitroxide diene 21 may be converted to a bifunctional molecule by linking a chemically reactive functional group to the diene tail by Diels-Alder chemistry, such as an isothiocyanate moiety, as described in the next section.

E. Diels-Alder Conversion of the Diene Tail to an Isothiocyanate Moiety Reactive with Proteins and Other Targets Containing Primary Amines Once an amplifier molecule has been converted to a pharmacologically active form, it may be rendered bifunctional via a reaction at the diene tail thereof. A "bifunctional" molecule possesses at least two differentially reactive groups. Such molecules for purposes of the present invention possess pharmacologically active groups as first differentially reactive groups, and at least one non-pharmacologically reactive moiety at a second differentially reactive group conferring on the molecule the ability to react with an extraneous group, thereby resulting in the covalent bonding of the bifunctional molecule to the extraneous group. The reaction to achieve bifunctionality should be conducted last. Otherwise, a reactive group on the tail might also react with the pharmacologically active groups during the synthesis procedure, leaving no reactive group for conjugation to the targeting molecule. The beauty of the 1,3-diene tail is that much other chemistry can take place, such as attaching pharmacologically active groups, without affecting the 1,3-diene. Then, at the end of the synthesis procedure, the selectivity of the Diels-Alder reaction is employed to attach a reactive group to the 1,3-diene without affecting the pharmacologically active groups or other parts of the molecule.

As used herein, a Diels-Alder adduct is any group on a molecule resulting from the Diels-Alder reaction of an appropriate dienophile with a conjugated diene group on the molecule.

As an example of the Diels-Alder reaction, to a stirred solution of pyrrolidine nitroxide diene 21 (32.3 mg, 10.0 μmol) in 1 mL acetonitrile was added N-(4-aminophenyl)maleimide (1.88 mg, 10.0 μmol). N-(4-aminophenyl)maleimide, known as a type of dienophile, is described in Keana et al., *J. Am. Chem. Soc.* 108:7957 (1986). The solution was refluxed ($N_2$) for 1 day. TLC analysis showed that all of the starting dienophile had been consumed and a single product had formed. Evaporation of the solvent gave the pyrrolidine nitroxide Diels-Alder adduct 22 (34 mg, 100% yield) as a thick yellow oil which was sufficiently pure for the next reaction: IR (neat) 3380, 1710, 1644, 1612, 1520, 1114 $cm^{-1}$. Analysis calculated for $C_{179}H_{317}N_{21}O_{41}\cdot 3H_2O$: C, 61.89; H, 9.37; N, 8.47; found: C, 61.78; H, 9.11; N, 8.36.

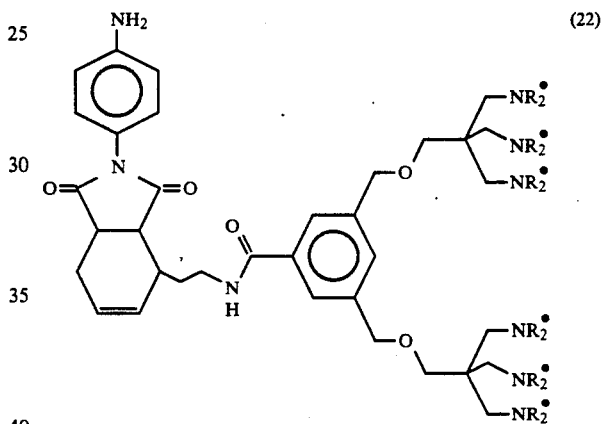

(22)

wherein R' is

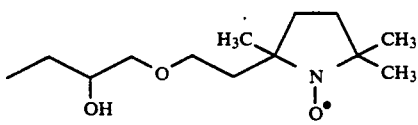

As is well known, maleic anhydride and its derivatives, such as N-(4-aminophenyl)maleimide, are particularly useful in Diels-Alder syntheses because of the doubly-bonded carbons in the 5-membered ring combined with the electron-withdrawing behavior of the anhydride. However, a large number of other dienophiles may also be combined via the Diels-Alder reaction with conjugated dienes. Hence, the bifunctional tail resulting from a Diels-Alder synthesis occurring on a 1,3 diene such as compound 21 can vary greatly depending upon the dienophile used. Because of the high specificity of the Diels-Alder reaction, it would not affect, and would be unaffected by the presence of, pharmacologically active groups attached to the amines so long as such groups do not have a diene structure capable of participating in the Diels-Alder reaction.

In compound 22, because the anilino nitrogen atom is relatively inert and therefore conferring limited utility as such in a bifunctional molecule, it should be converted to the much more reactive isothiocyanate, which is still reasonably stable in water at pH 7, by the following procedure: 75 mL thiophosgene in chloroform 0.2N, 15 μmol) was added to a stirred solution of the nitroxide Diels-Alder adduct 22 (53 mg, 15 μmol) and sodium acetate (4.1 mg, 50 μmol) in 1 mL MeOH at 0° C. The mixture was stirred further at 0° C. for 5 min, diluted with chloroform, then washed with water. The chloroform solution was dried (MgSO$_4$) and evaporated to give a light yellow oil which was chromatographed over silica gel. Elution with 10:1 CHCl$_3$:MeOH, followed by 5:1 CHCl$_3$:MeOH, then by 5:1:0.1 CHCl$_3$:MeOH:Et$_3$N, gave the nitroxide isothiocyanate (compound 23) (37 mg, 71% yield) as a thick yellow oil: IR (film) 3353, 2187, 2105, 1711, 1650, 1604, 1542, 1509, 1118 cm$^{-1}$: Analysis calculated for C$_{180}$H$_{315}$N$_{21}$O$_{41}$S.3H$_2$O: C, 61.49; H, 9.20; N, 8.37; S, 0.91; found: C, 61.41; H, 8.95; N, 7.97; S, 0.92.

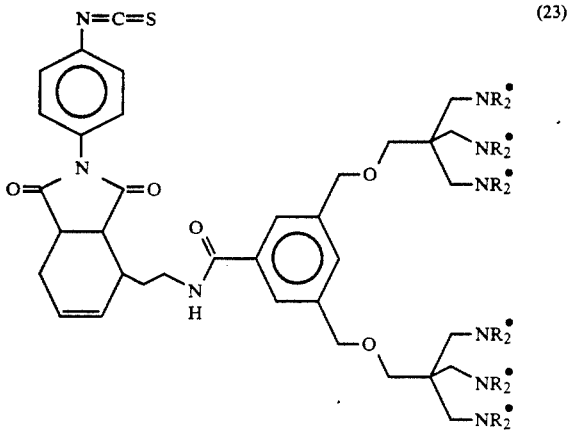

(23)

wherein R' is

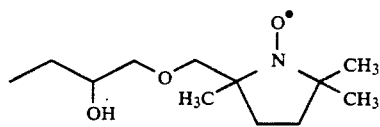

The isothiocyanate (—N=C=S) moiety is particularly reactive with exposed terminal amines such as the ε-amino terminus of the amino acid lysine found in many proteins, including immunoglobulins-(antibodies), forming a thiourea (—NHSNH—) linkage of a compound such as 23 with lysine. As used herein, "exposed" simply means available for binding; the moiety is not already participating in another bond, or is not stereochemically or conformationally obstructed within the molecule. Since isothiocyanate is reactive with terminal amines in general, compounds such as 23 having an isothiocyanate moiety can also be attached via similar chemistry to, for example, polylysine, polyethylamine, and other polyamines. Such attachment to non-protein polymers yields amplified molecules having a very large number of pharmacologically active groups attached thereto. An experiment confirming the requisite chemistry is described later in this specification (section L).

Further, compounds such as 23 can also be attached by a thiourea linkage to liposomes as described in the co-pending parent application (Ser. No. 06/928,943), such attachment occurring at terminal amine moieties extending outward from the surface thereof.

Hence, amplified molecules such as compound 23 having an isothiocyanate moiety can be chemically linked to monoclonal antibodies specific for a physiological or anatomical target of interest. For example, amplified molecules containing a multiplicity of any of various stable nitroxides can be attached as above to monoclonal antibodies specific for target tumor cells that the physician wants to non-surgically locate in a patient's body using MRI. Since each amplified molecule has a multiplicity of MRI contrast-enhancing groups, fewer amplified molecules need to be linked to each antibody molecule to achieve the desired contrast enhancement. Linking fewer molecules to the antibody prevents undesired changes in the structure of the antibody, which otherwise may alter the binding specificity of the antibody or destroy its binding activity altogether.

As used herein, a targeting molecule is any molecule according to the present invention that preferentially binds to a specific anatomical or physiological site (target) in or on the body. Generally, the target possesses a particular chemical entity, such as a particular type of protein molecule or portion thereof, to which the targeting molecule preferentially, if not exclusively, binds. For example, a monoclonal antibody conjugate may bind to a specific receptor on a specific type of cell. In the case of the other amplifier assemblies such as liposomes, selective targeting may be achieved based on the ability of a certain tissue or organ (the liver, for example) to take up the liposome.

It is also expected that the amino group on the nitroxide Diels-Alder adduct 22 can be diazotized to render it reactive with a tyrosine residue through diazo coupling chemistry.

Note that the isothiocyanate group on compound 23 is attached to a ring system generated as a consequence of the Diels-Alder reaction used to attach the reactive group. One possible advantage of this ring system is that it contains a cyclohexene carbon-carbon double bond. This site may serve as a means to introduce a tritium label of high specific activity through catalytic tritiation, should one desire to have a tritiated analog of this and similar compounds. Should the sulfur atoms cause problems in the tritiation step, it might be possible to add tritium using any number of other techniques. The double bond may be iodinated with radioactivate iodine as well.

In order to characterize the chemistry of the synthetic pathway from the nitroxide hexaamine 17 to the nitroxide diene 21, and to confirm the reactivity of the isothiocyanate moiety on nitroxide 23 with an amine site on a target biomolecule, it was necessary to convert the compounds to a suitable diamagnetic, rather than paramagnetic form. In particular, the NMR spectral lines tend to be quite broad when paramagnetic species such as nitroxides are present on a molecule. A diamagnetic series of compounds allowed the use of high-field (high-resolution) NMR spectroscopy in structural analysis. Synthesis of the diamagnetic forms was as follows: A solution of hexaamine 17 (19.6 mg, 0.040 mmol) in 1.5 mL EtOH was added to a stirred solution of 4-methoxyphenyl isothiocyanate (66 mg, 0.40 mmol) in 5 mL of 1:1 EtOH:CHCl$_3$. 4-Methoxyphenylisothiocyanate was used because it had an easily distinguishable methoxy group in the NMR spectrum. After 1 h at 25° C., the mixture was filtered and the filtrate was evaporated.

The residue was chromatographed over silica gel. Elution with 50:1 CHCl₃:MeOH gave the thiocarbamate (compound 24) (46 mg, 77% yield) as a white solid. Crystallization from EtOH afforded the analytical specimen as white crystals: mp 144°–147° C.; IR 3412, 3200, 1657, 1608, 1542, 1511 cm$^{-1}$; NMR δ 2.43 (q, 2), 3.21 (s, 4), 3.49 (brd, 12), 3.50 (t, 2), 3.79 (s, 18), 4.26 (s, 4), 5.04 (dd, 2), 5.72 (m, 1), 6.10–6.35 (m, 2), 6.99 (ABq, 24), 7.45 (brs, 12), 7.64 (s, 2). Analysis calculated for $C_{73}H_{87}N_{13}O_9S_6 \cdot H_2O$: C, 58.42; H, 5.97; N, 12.13; found: C, 58.04; H, 5.81; N, 12.15.

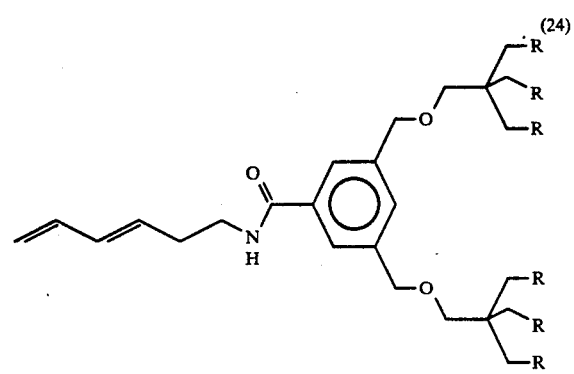

(24)

wherein R is

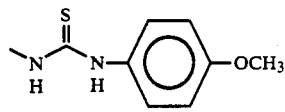

N-(4-isothiocyanatophenyl)maleimide (compound 25) (4.0 mg, 0.017 mmol) was added to a solution of thiocarbamate 24 (20.0 mg, 0.0135 mmol) in 1 mL acetone. N-(4-isothiocyanatophenyl)maleimide is described in Keana et al., *J. Am. Chem. Soc.* 108:7957 (1986). After a 2 h reflux period, the solvent was evaporated and the residue was purified by preparative TLC. Elution with 100:4:3 CHCl₃:MeOH:acetone gave the Diels-Alder adduct (compound 26) (13 mg, 56% yield) as a white solid: mp 155°–159° C.; IR 3412, 3200, 2117, 2062, 1711, 1651, 1608, 1542, 1511 cm$^{-1}$; NMR 2.20 (m, 3), 2.28–2.50 (m, 2), 3.23 (s, 4), 3.49 (brs, 12), 3.50–3.60 (m, 2), 3.79 (s, 18), 4.25 (s, 4), 5.80–6.02 (m, 2), 6.96 (ABq, 24), 7.35 (ABq, 4), 7.45 (brs, 6), 7.56 (brs, 6), 7.70 (s, 2). Analysis calculated for $C_{84}H_{93}N_{15}O_{11}S_7 \cdot 4H_2O$: C, 56.51; H, 5.70; N, 11.77; found: C, 56.38; H, 5.26; N, 11.48.

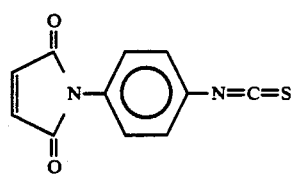

(25)

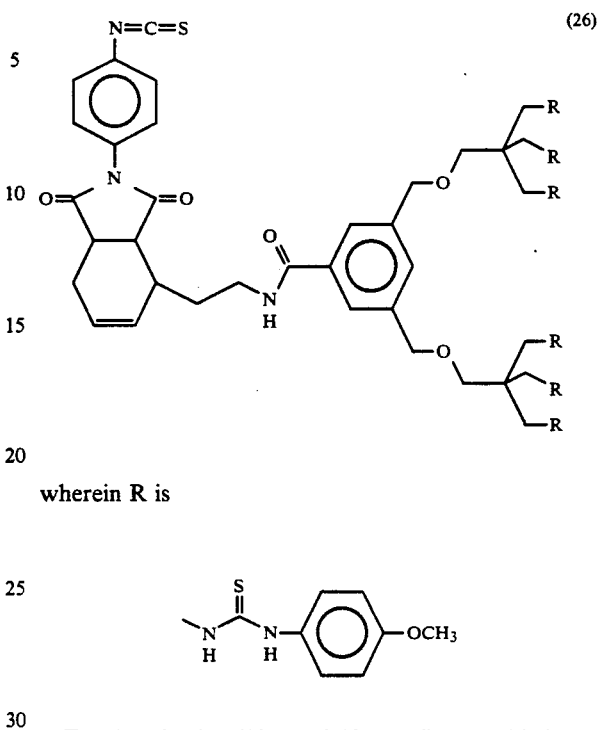

(26)

wherein R is

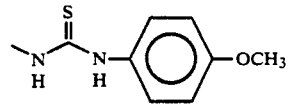

Tert-butylamine (10 mg, 0.13 mmol) was added to a solution of isothiocyanate 26 (6.0 mg, 3.5 lmol) in 1 mL CHCl₃. This somewhat hindered amine with a characteristic NMR spectrum (one sharp singlet together with the NH protons) was chosen to demonstrate the ability of the newly introduced isothiocyanate group in compound 26 to react with an amine, modeling an amine site on a biomolecule. After 2 h at 25° C., the solvent was removed and the residue was purified by preparative TLC. Elution with 6:1 ethyl acetate:hexanes gave the thiocarbamate 27 (5.0 mg, 80% yield) as a white solid: mp 161°–165° C.; NMR δ 1.58 (s, 9), 2.2 (m, 3), 2.26–2.55 (m, 2), 3.20 (s, 4), 3.27 (t, 2), 3.49 (brd, 12), 3.50–3.70 (m, 2), 3.79 (s, 18), 4.25 (s, 4) 5.81–6.03 (m, 2), 6.97 (ABq, 24), 7.24 (ABq, 4), 7.44 (brs, 6), 7.60 (brs, 6), 7.71 (s, 2). Analysis calculated for $C_{88}H_{104}N_{16}O_{11}S_7 \cdot 3H_2O$: C, 57.43; H, 6.02; N, 12.18; found: C, 57.84; H, 6.01; N, 11.53. The reaction from the isothiocyanate 26 to the thiocarbamate 27 is analogous to the reaction of, for example, the nitroxide isothiocyanate 23 with a lysine residue on a target, protein, or with primary amines on polylysine, polyethyleneimine, polyamine, and any of a number of other molecules containing one or more exposed primary amino groups.

(27)

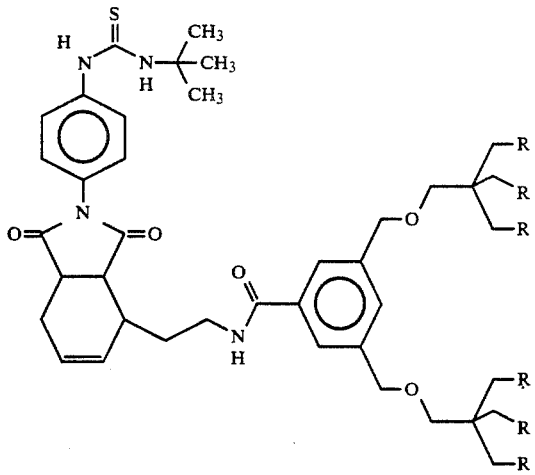

wherein R is

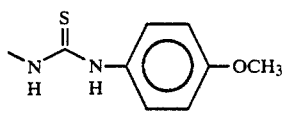

F. Synthesis of an Amplifier Molecule with Amplification Factor of Six from 3-Audio-2,2-bis(azidomethyl)-1-propanol To a stirred mixture of 3-azido-2,2-bis(azidomethyl)-1-propanol (compound 8) (633 mg, 3.00 mmol), 2 mL of 50% w/w aqueous NaOH, and a 0° C. mixture of tetrabutylammonium hydrogen sulfate (50 mg) and 1.2 mL epichlorohydrin (1.44 g, 15.5 mmol) were added. The resulting mixture was stirred at 25° C. for 3 h, poured onto ice, and extracted with ether. The extract was washed with water, then with brine, dried (MgSO4), and evaporated to give an oil that was chromatographed over silica gel. Elution with 5:1 hexane:ethyl acetate gave 2-[1-(3-azido-2,2-bis(azidomethyl)propyl)oxymethyl]-oxirane (compound 28) (741 mg, 92% yield) as a colorless oil: IR (film) 2108, 1451, 1302, 1105 cm$^{-1}$; NMR δ 2.58 (dd, 1), 2.81 (dd, 1), 3.15 (m, 1), 3.33 (dd, 1), 3.35 (s, 6), 3.79 (dd, 1); —C NMR δ 43.97 (Cl), 44.79 (C6), 50.50 (C2), 51.60 (CH2N3), 69.82 (C5), 72.36 (C3).

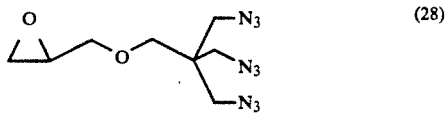

(28)

Epoxyazide 2B (160.2 mg, 0.600 mmol) was added to a solution of 3,5-hexadienylamine (compound 14) 19.4 mg, 0.200 mmol) in 2 mL EtOH. The solution was refluxed for 12 h, followed by removal of the solvent. The residue was chromatographed over silica gel. Elution with 10:7 hexane:ethyl acetate gave essentially pure (by NMR) N,N-bis[1-(7-azido-2-hydroxy-4-oxa-6,6-bis-(azidomethyl))heptyl]-(E)-1-hexa-3,5-dienylamine (compound 29) (69 mg, 55% yield) as a colorless oil: IR (film) 3402, 1651, 1603, 1451, 1300, 1118, 1008 cm$^{-1}$; NMR δ 2.26 (q, 2), 2.56 (m, 4), 2.65 (t, 2), 3.35 (s, 12), 3.36 (s, 4), 3.45 (m, 4), 3.84 (m, 2), 5.07 (dd, 2), 5.65 (m, 1), 6.06–6.37 (m, 2).

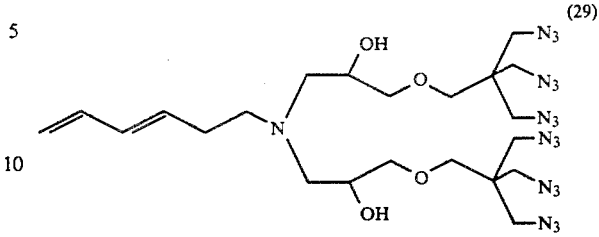

(29)

Triphenylphosphine (210 mg, 0.80 mmol) was added to a stirred solution of hexaazide 29 (63.1 mg, 0.10 mmol) in 3 mL dry THF. After 2 h water (72 mg, 4.0 mmol) was added and the mixture refluxed for 12 h. The mixture was then cooled, diluted with 5 mL water, and extracted with ether. The aqueous phase was evaporated to dryness to give essentially pure (by NMR) N,N-bis[1-(7-amino-2-hydroxy-4-oxa-6,6-bis(aminomethyl))heptyl]-(E)-1-hexa-3,5-dienylamine (compound 30) (43 mg, 90% yield) as a light yellow oil: IR (film) 3600-2800, 1651, 1603, 1462, 1364, 1324, 1120, 1008 cm$^{-1}$; NMR (D2O) δ 2.24 (q, 2), 2.56 (s, 12), 2.60 (m, 4), 2.62 (t, 2), 3.38 (s, 4), 3.43 (m, 4), 3.90 (m, 2), 5.06 (dd, 2), 5.73 (m, 1), 6.11–6.42 (m, 2). The hexaamine 30 is a novel amplifier molecule with an amplification factor of six, and a diene tail which can be either left unchanged or used to attach a functional moiety such as isothiocyanate via Diels-Alder chemistry.

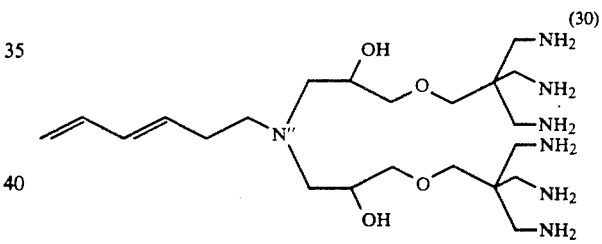

(30)

To facilitate elemental analysis of the hexaamine 30, it was converted to the toluenesulfonate salt by the following procedure: A solution of hexaamine 30 (9.5 mg, 0.02 mmol) in 1 mL EtOH was added to a solution of p-toluenesulfonic acid monohydrate (26.6 mg, 0.14 mmol) in 1 mL EtOH. Then, ether was added and the solution was allowed to stand at −10° C. overnight. The crystals were collected, washed with acetone, washed with ether, and dried, giving 24 mg (71% yield) of the heptatoluene-sulfonate salt as a white hygroscopic solid: mp 220°-225° C. (dec); NMR (D2O) δ 2.35 (s, 21), 2.49 (q, 2), 3.30 (s, 12), 3.34 (m, 4), 3.53 (t, 2), 3.60 (m, 4), 3.75 (s, 4), 4.30 (m, 2), 5.15 (dd, 2), 5.59 (m, 1), 6.10–6.30 (m, 2), 7.43 (ABq, 28). Analysis calculated for C71H105N7O25S7. 2H2O: C, 49.66; H, 6.40; N, 5.71; found: C, 49.54; H, 6 44; N, 5.85.

G. Synthesis of Novel Gadolinium Complexing Compounds from Diethylenetriaminepentaacetic Acid (DTPA)

DTPA and the novel analogs described herein represent another class of MRI contrast-enhancing agents because of their ability to capture Gd$^{3+}$ and concentrate the ion in anatomical sites of interest. Although other paramagnetic metal cations can effect sufficient spin relaxation to serve as MRI contrast enhancers, $Gd^{3+}$ has the highest relaxation-rate enhancement property of all such cations. DTPA is presently the favored ligand for $Gd^{3+}$ because it has a relatively high dissociation constant $(K_a)$, where log $K_1=22$. As a result, $Gd^{3+}$-DTPA is presently widely used in biology as an MRI contrast-enhancing agent. Actually, virtually any paramagnetic metal ion chelate (such as EDTA) having a stability constant approaching or exceeding that of $Gd^{3+}$-DTPA is useful as an MRI contrast enhancer. Such a chelate is also a useful group to amplify according to the present invention.

Starting with DTPA, we have synthesized a number of Gd-complexing agents that are superior to DTPA in that they contain an additional chemically reactive group useful for attaching the chelate to an amplifier molecule or other target site. The synthesis steps were as follows:

Thionyl chloride (11.9 g, 0.10 mol) was added dropwise at 0° C. to a stirred suspension of DTPA (compound 31) (3.93 g, 0.01 mol) in 100 mL MeOH. The resulting solution was stirred at 25° C. overnight, followed by removal of most of the solvent. The residue was treated with saturated aqueous $NaHCO_:$, then extracted with ether. The extract was dried $(MgSO_4)$ and evaporated to give pentamethyl diethylenetriaminepentaacetate (compound 32) (3.75 g, 81% yield) as a colorless oil: IR (film) 1743, 1437, 1203 $cm^{-1}$; NMR δ 2.75–2.87 (m, 8), 3.49 (s, 2), 3.59 (s, 8), 3.68 (s, 3), 3.70 (s, 12). Analysis calculated for $C_{19}H_{33}N_3O_{10}\cdot H_2O$: C, 47.40; H, 7.33; N, 8.73; found: C, 47.24; H, 6.94; N, 8.52.

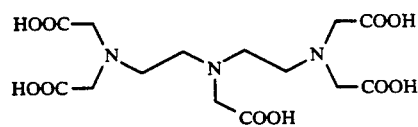
(31)

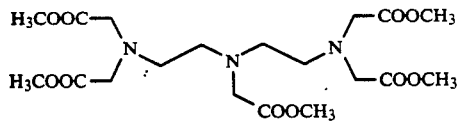
(32)

A solution of 85% KOH pellets (0.330 g, 5.0 mmol) in 1 mL MeOH was added to a stirred solution of pentaester 32 (2.315 g, 5.0 mmol) in 5 mL MeOH at 0° C. After 24 h at 25° C., the solvent was removed and the residue was chromatographed over silica gel. Elution with 6:1 $CH_2Cl_2$:MeOH first gave starting pentaester 32 (0.55 g, 24% yield) and then the tetramethyl diethylenetriaminepentaacetate potassium salt (compound 33) (1.54 g, 63% yield, possibly containing cations other than $K^+$ owing to ion exchange on the silica gel) as a colorless oil suitable for the next reaction: IR (film) 2530, 1743, 1637, 1603, 1440, 1216, 1010 $cm^{-1}$; NMR δ 2.80–2.97 (m, 8), 3.47 (s, 2), 3.52 (s, 2), 3.56 (s, 4), 3.61 (s, 2), 3.70 (s, 6), 3.71 (s, 3), 3.72 (s, 3).

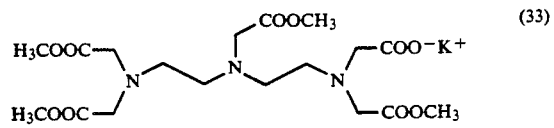
(33)

The next step in the synthesis can occur in either of two ways. The preferred method is as follows: To a stirred solution of salt 33 (488 mg, 1.0 mmol) in 5 mL dry DMF at 0° C. were added 4-nitro-DL-phenylalanine methyl ester hydrochloride (261 mg, 1.0 mmol) and N,N'-dicyclohexylcarbodiimide (227 mg, 1.1 mmol). The solution was stirred at 25° C. for 2 days. The solution was diluted with 25 mL EtOAc-ether and filtered. The filtrate was washed with saturated aqueous $NaHCO_3$, then with water, followed by extraction with 1N aqueous HCl. The aqueous phase was extracted with $CHCl_3$. The extract was washed first with water, then with saturated aqueous $NaHCO^3$, then with water again. The extract was then dried $(MgSO_4)$, and evaporated to give dimethyl 2-(4-nitrobenzyl)-3,6,9,12-tetraaza-4-oxo-6,9,12-tri(methoxycarbonylmethyl)-tetradecanedioate (compound 34) (504 mg, 77% yield) as a light yellow oil.

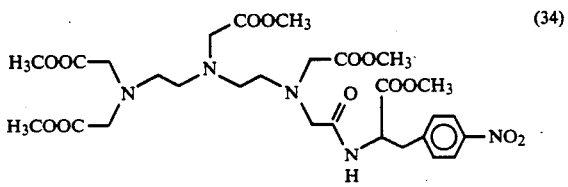
(34)

The alternative method of synthesizing the pentaester 34 is less preferred because of the method's greater complexity and lesser percent yield of pentaester 34. The alternative procedure is as follows: To a stirred solution of DTPA (compound 31) (393 mg, 1.0 mmol) in 10 mL dry DMF at 0° C. were added 4-nitro-DL-phenylalanine methyl ester (compound 35) (210 mg, 1.0 mmol) and N,N'-dicyclohexylcarbodiimide (227 mg, 1.1 mmol). The solution was stirred at 25° C. overnight and then filtered. The filtrate was evaporated to dryness in vacuo. The white solid residue was dissolved in 20 mL MeOH. At 0° C. thionyl chloride (1.19 g, 10.0 mmol) was added dropwise. The mixture was stirred at 25° C. overnight and then concentrated to dryness. The residue was dissolved in water and filtered. The filtrate was extracted with $CHCl_3$. The extract was washed with saturated aqueous $NaHCO_3$ and evaporated to dryness to give an oil (454 mg) that was a mixture of pentaester 34 and dimethyl 2,16-(4-nitrobenzyl)-3,6,9,12,15-pentaaza-4,14-dioxo-6,9,12-tri(methoxycarbonylmethyl)-heptaedecanedioate (compound 36), as determined by TLC. After the $CHCl_3$ extraction, the aqueous phase was basified with $NaHCO_3$ and extracted with $CHCl_3$. The extract was dried $(MgSO_4)$ and evaporated to give the starting pentaester 32 (134 mg, 29% yield).

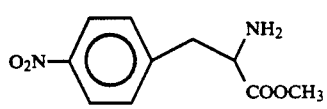
(35)

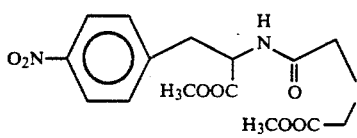
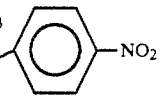

(36)

The mixture of compounds 34 and 36 (454 mg) was chromatographed over silica gel. Elution with 35:15 ether:THF gave the pentaester 34 (190 mg, 29% yield) as a light yellow oil: IR (film) 3332, 1742, 1675, 1607, 1523, 1437, 1348, 1205, 1013 cm$^{-1}$; NMR δ 2.70–2.84 (m, 8), 3.17–3.30 (m, 2), 3.26 (s, 2), 3.36 (s, 2), 3.37 (s, 2), 3.55 (s, 4), 3.67 (s, 3), 3.69 (s, 9), 3.73 (s, 3), 4.84–4.92 (m, 1), 7.39–9.20 (ABq, 4); MS m/e 657 (0.6) (M$^+$ +1), 626 (0.4), 597 (4.8), 481 (40), 289 (100), 188 (63), 174 (33). Analysis calculated for $C_{28}H_{41}N_5O_{13}$: C, 51.29; H, 6.30; N, 10.68; found: C, 53.07; H, 6.73; N, 9.60.

Continued elution gave compound 36 (129 mg, 7% yield based on compound 35) as a yellow oil: IR (film) 3332, 1743, 1675, 1607, 1521, 1436, 1348, 1209, 1003 cm$^{-1}$; NMR δ 2.60–2.75 (m, 8), 3.15–3.40 (m, 4), 3.22 (s, 2), 3.31 (s, 8), 3.67 (s, 3), 3.68 (s, 6), 3.73 (s, 6), 4.85–4.95 (m, 2), 7.36–8.17 (ABq, 8). Analysis calculated for $C_{37}H_{49}N_7O_{16}$: C, 52.42; H, 5.83; N, 11.56; found: C, 52.92; H, 6.15; N, 10.67. Besides being a by-product of this synthesis procedure, compound 36 may be useful as a new crosslinking agent after introduction of an isothiocyanate group at each end, using the same chemistry as described herein.

Once the pentaester 34 was obtained by either method above, the synthesis continued as follows: Five mL of 1N aqueous NaOH was added to a solution of pentaester 34 (655 mg, 1.0 mmol) in 10 mL MeOH. The solution was allowed to stand at 5° C. overnight followed by addition of 5 mL of 1N aqueous HCl. The resulting pH 2 solution was evaporated and the residue dissolved in MeOH and evaporated to dryness. This was repeated three times. The resulting yellowish solid was suspended in glacial acetic acid, warmed to 45° C., and filtered to remove the NaCl. The filtrate was diluted with benzene and acetone. The resulting precipitate was washed with acetone, then ether, and dried to give 2-(4-nitrobenzyl)-3,6,9,12-tetraaza-4-oxo-6,9,12-tri(carboxymethyl)-tetradecanedioic acid (compound 37) (403 mg, 69% yield) as a light yellow powder: mp 170°–174° C.; IR (nujol) 2360–3600, 3346, 1730, 1686, 1645, 1608 cm$^{-1}$; NMR (D$_2$O) δ 3.10–3.45 (m, 8), 3.37–3.55 (m, 2), 3 50 (s, 2), 3.62 (s, 2), 3.79 (s, 2), 3.88 (s, 4), 7.44–8.17 (ABq, 4). Analysis calculated for $C_{23}H_{31}N_5O_{13}\cdot 2.5H_2O$: C 43.81; H 5.76; N 11.11; found: C, 43.85; H, 5.36; N, 10.82.

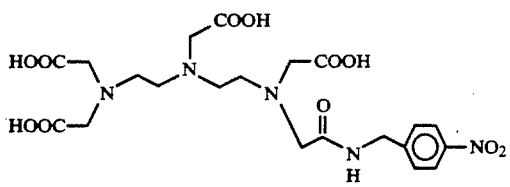

(37)

To a solution of nitro derivative 37 (117 mg, 0.20 mmol) in 5 mL D$_2$O were added 0.8 mL of 1N NaOH in D$_2$O (0.80 mmol) and 10 mg of 30% Pd/C. The suspension was stirred under 1 atmosphere of H$_2$ gas at 25° C. for 3 h (reaction complete by NMR). The mixture was filtered and the stirred filtrate was treated with a solution of thiophosgene (28.5 mg, 0.25 mmol) in 5 mL CHCl$_3$. After 15 min (negative Ehrlich test), the organic phase was separated and the aqueous phase was washed with CHCl$_3$. The aqueous phase was concentrated to 1/5 the original volume and the pH adjusted to 1.5 by addition of 1N HCl. The precipitated oil was rinsed with water, dissolved in MeOH, evaporated, and redissolved in MeOH. Ether was added, causing 2-(4-isothiocyanatobenzyl)-3,6,9,12-tetraaza-4-oxo-6,9,12-tri(carboxymethyl)-tetradecanedioic acid (compound 38) (47 mg, 39% yield) to precipitate as a white solid: mp 140°–180° C. (dec); IR (nujol]2360–3600, 3352, 2178, 2102, 1731, 1683, 1643, 1543 cm$^{-1}$; NMR (D$_2$O) δ 2.90–3.35 (m, 2), 3.05–3.45 (m, 8), 3.54 (s, 2), 3.60 (s, 2), 3.82 (s, 2), 3.88 (s, 4), 7.25 (s, 4). Analysis calculated for $C_{24}H_{31}N_5O_{11}S\cdot H_2O$: C, 46.82; H, 5.40; N, 11.38; found: C, 47.08; H, 5.39; N, 11.26. Evaporation of the aqueous phase yielded additional amounts of compound 38 (101 mg, 40%) contaminated with NaCl.

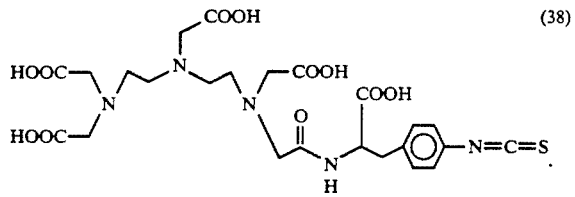

(38)

The isothiocyanate 38 is a novel compound representing an appreciable improvement over the existing Gd-complexing MRI contrast enhancers DTPA and "DTPA dianhydride" (compound 39) which are presently the only widely used means of attaching a DTPA-like residue to a biomolecule. Note that the isothiocyanate group was introduced in a completely different way than the Diels-Alder chemistry utilized with other compounds described herein. One advantage of compound 38 over compound 39 is that compound 38 is monovalent and compound 39 is divalent. Another advantage of compound 38 is the more moderated reactivity of the isothiocyanate group over the anhydride group in aqueous media. Substantial excesses of the dianhydride 39 are normally used because so much is "lost" by unproductive reaction with water. This generates a potential separation problem after the attachment reaction is completed. Yet another advantage of isothiocyanate 38 is that the essential coordinating carboxylic acid groups (all five of them) are preserved. This tends to lead to a more stable metal complex than when one of the carboxylic groups has been changed into an amide group, as happens when dianhydride 39 is used with an amine-containing target molecule.

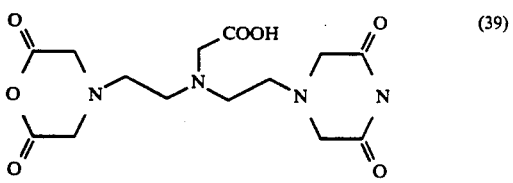

(39)

Both DTPA and DTPA dianhydride must be used in relatively high concentration to ensure complexing of sufficient amounts of $Gd^{3+}$ to produce the desired MRI image contrast. Also, DTPA lacks a reactive moiety that would enable the molecule to attach to a target or targeting biomolecule. Further, DTPA dianhydride, when used in the required excess concentration to produce adequate image contrast, tends to undergo cross-linking which reduces the Gd-chelating capacity of the molecule, requiring an excess dose to the patient of Gd. Isothiocyanate 38 is a "functionalized DTPA" with only a single reactive moiety, thereby eliminating cross-linking between molecules. Compound 38 also retains the same number of carboxyl groups as DTPA, enabling compound 38 to complex as much $Gd^{3+}$ as DTPA. The isothiocyanate moiety enables compound 38 to attach to target biomolecules, thereby effecting a greater concentration of gadolinium for superior MRI image contrast at the anatomical site of interest.

A compound superior to isothiocyanate 38 in its ability to complex gadolinium was synthesized by converting the pentaester 34 into a gadolinium complex disodium salt, according to the following procedure: A mixture of the nitro pentaester 34 (492 mg, 0.75 mmol) and 30% Pd/C (200 mg) in 30 mL MeOH was stirred under 1 atmosphere of $H_2$ gas for 3 h. Filtration and evaporation of the filtrate gave pure (by TLC) dimethyl 2-(4-aminobenzyl)-3,6,9,12-tetraaza-4-oxo-6,9,12-tri(-carboxymethyl)tetradecanedioate (compound 40) (460 mg, 98% yield) as a colorless oil: IR (film) 3360, 1743, 1672, 1631, 1517, 1435, 1207, 1011 cm$^{-1}$; NMR δ 2.60–2.85 (m, 8), 2.94–3.11 (m, 2), 3.27 (s, 2), 3.38 (s, 4), 3.56 (s, 4), 3.68 (s, 3), 3.688 (s, 3), 3.692 (s, 6), 3.71 (s, 3), 4.71–4.79 (m, 1), 6.59–6.94 (ABq, 4), 7.83 (d, 1).

A solution of LiOH.H$_2$O (50.3 mg, 1.20 mmol) in 1 mL water was added to a solution of amino pentaester 40 (150 mg, 0.24 mmol) in 5 mL MeOH. After 3 h at 25° C., the solution was evaporated to dryness to give a light yellow powder. The powder was dissolved in 10 mL MeOH and treated with 1.20 mL of a solution of 0.2 M thiophosgene in CHCl$_3$(0.24 mmol). After 5 min, the mixture was concentrated to dryness, giving 2-(4-isothiocyanatobenzyl)-3,6,9,12-tetraaza-4-oxo-6,9,12-tri(carboxymethyl)-tetradecanedioic acid trilithium salt (compound 41) (177 mg, 100%) as a yellow powder suitable for the next reaction: IR (nujol) 3383, 2178, 2117, 1670, 1599, 1505, 1412, 1337, 1121, 931 cm$^{-1}$; NMR (D$_2$O) δ 2.80–3.30 (m, 10), 3.38 (s, 2), 3.45 (s, 4), 3.82 (s, 4), 4.47–4.53 (m, 1), 7.26 (s, 4).

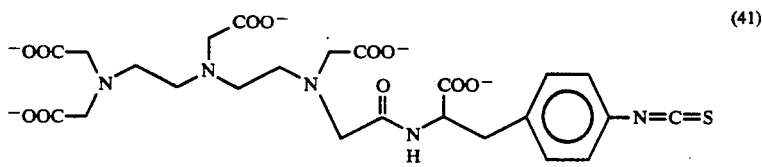

(41)

The lithium salt is preferable to, say, the sodium salt for use in this synthesis procedure because of its solubility in acetone and methanol. The sodium salt is not sufficiently soluble in either solvent.

A solution of GdCl$_3$.6H$_2$O (74.3 mg, 0.20 mmol) in 2 mL MeOH was added to a stirred solution of isothiocyanate lithium salt 41 (150 mg, 0.20 mmol) in MeOH (2 mL). The resulting cloudy mixture containing a white precipitate was treated with a solution of NaOH (16.0 mg, 0.40 mmol) in 1 mL MeOH. A clear solution with pH 6.5 resulted. Then, 25 mL acetone was added and the precipitate was collected and washed with acetone. The resulting light yellow powder was suspended in water and filtered. The colorless filtrate was evaporated to dryness and the residue was dissolved in MeOH and evaporated to dryness. The residue was suspended in ether-acetone and collected by filtration, giving 2-(4-isothiocyanatobenzyl)-3,6,9,12-tetraaza-6,9,12-(carboxymethyl)-tetradecanedioic acid gadolinium complex disodium salt (compound 42) (145 mg, 91% yield) as a white powder: IR (nujol) 3350, 2176, 2102, 1597, 1505, 1405, 1331, 1094, 934 cm$^{-1}$. Analysis calculated for C$_{24}$H$_{26}$N$_5$O$_{11}$SNa$_2$Gd.3H$_2$O: C, 33.92; H, 3.79; N, 8.24; S, 3.77; found: C, 33.89; H, 3.40; N, 8.50; S. 3.14.

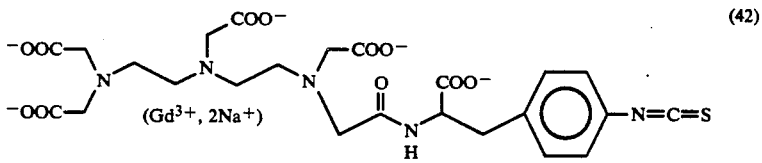

(42)

Complex 42 is superior to the isothiocyanate 38 in its ability to chelate $Gd^{3+}$. In addition to having the reactive isothiocyanate group as in compound 38, complex

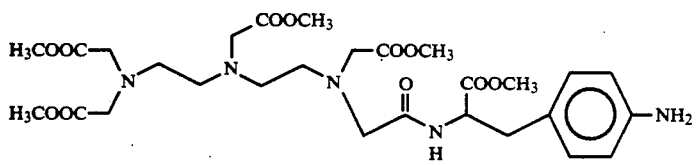

(40)

42 also has stoichiometric amounts of $Gd^{3+}$ complexed thereto, whereas compound 38 does not. Compound 42 is also monovalent. Complex 42 is a bifunctional $Gd^{3+}$ complex that can attach to sites on biomolecules and cells, especially primary amine sites. A representative reaction would be that of the isothiocyanate moiety with the terminal amine on lysine, as described supra. The sodium cations associated with complex 42 serve a charge-balancing role.

H. Conversion of Hexaamine 17 Into a Six-Branched Gadolinium Complexing Agent Synthesis of a six-branched $Gd^{3+}$-complexing agent from the hexaamine 17 was undertaken in part to demonstrate how various chelators may be linked to an amplifier molecule of the present invention. Such chelators are not restricted only to gadolinium chelators.

Because of its reactive isothiocyanate group, complex 42 can be bonded via a thiourea linkage to all six of the amino groups on the hexaamine 17. The ultimate result is a diene-tailed MRI contrast agent analogous to compound 23, but having a gadolinium-complexing group on each of the six branches rather than a pair of nitroxides. The thiourea linkage procedure is as follows:

A solution of complex 42 (51 mg, 0.060 mmol) in 0.5 mL $H_2$ was added to a stirred solution of hexaamine 17 (4.9 mg, 0.010 mmol) in 0.5 mL $H_2O$. The reaction mixture became turbid. One mL of MeOH was added and the resulting still turbid mixture was stirred at 25° C. for 30 min. A ninhydrin test for primary amines was negative and the pH changed from 10 to 7. The mixture was filtered and the clear filtrate was allowed to stand at 25° C. overniqht. The solvent was evaporated and the residue dissolved in MeOH and evaporated to dryness to give the hexathiourea diene gadolinium complex (compound 43) (50 mg, 95% yield) as a white powder (reverse phase TLC eluted with 5:1 water:$CH_3CN$ showed one major spot): IR (nujol) 3269, 1600, 1545, 1515, 1403, 1326, 1096, 934 cm$^{-1}$: Analysis calculated for $C_{169}H_{201}Gd_6N_{37}Na_{12}O_{69}S_6 \cdot 12H_2O$: C, 37.02; H, 4.14; N, 9.45; S, 3.51; found: C, 37.35; H, 4.32; N, 9.37; S, 2.89.

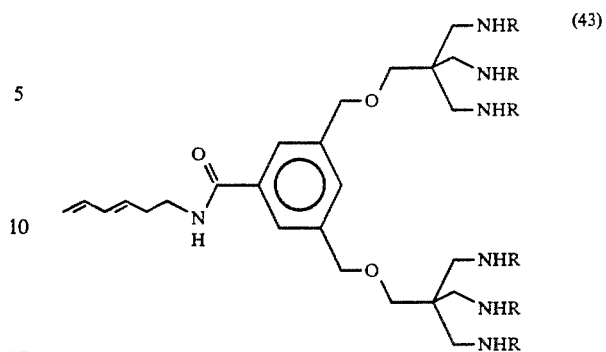

wherein R is

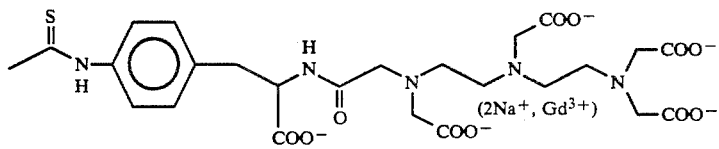

If desired, the complex 43 may be rendered bifunctional via a Diels-Alder addition at the 1,3-diene tail. As an illustrative example, N-(4-aminophenyl)-maleimide (0.94 mg, 0.0050 mmol) was added to a solution of complex 43 (21 mg, 0.0040 mmol) in 2 mL of 3:1 $CH_3CN$:water. N-(4-aminophenyl)-maleimide is described in Keana et al., *J. Am. Chem. Soc.* 108:7957 (1986). The resulting solution was refluxed with stirring overnight. The solvent was evaporated and the residue suspended in $CH_3CN$ and refluxed with stirring for 10 min. The suspension was cooled to 25° C. and filtered to give the Diels-Alder adduct 44 (19 mg, 87% yield) as a light yellow powder: IR (nujol) 3300, 1705, 1598, 1541, 1517, 1406, 1096, 933 cm$^{-1}$.

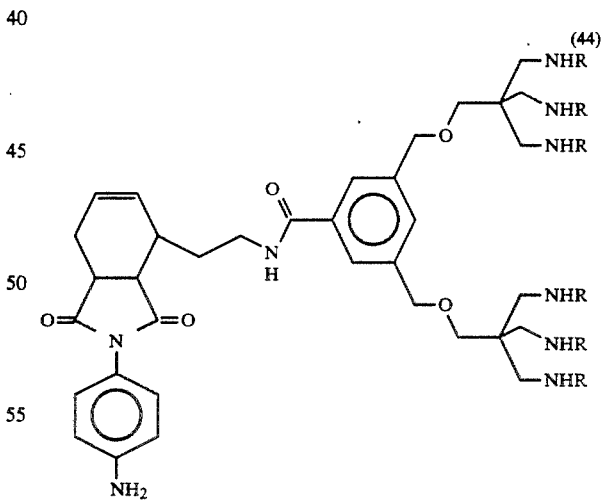

wherein R is

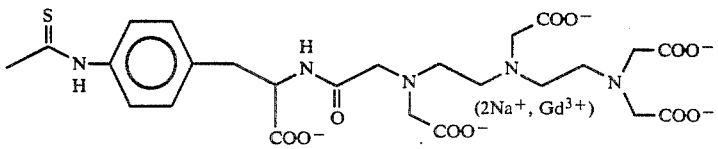

A 0.2N solution of thiophosgene in CHCl₃ (0.030 mL, 0.006 mmol) was added to a stirred solution of the Diels-Alder adduct 44 (10.9 mg, 0.0020 mmol) in 1.5 mL MeOH and water (3 drops water to achieve a solution). After 10 min (negative Ehrlich test), the pH was adjusted to 6.5 by the addition of LiOH in MeOH. The mixture was filtered and the filtrate was evaporated. The residue was suspended in MeOH and evaporated again. The residue was suspended in MeOH-acetone and filtered. The solid was washed with acetone and dried to give the isothiocyanate 45 (9 mg, 82% yield) as a white powder: IR (nujol) 3353, 2176, 2114, 1705, 1604, 1545, 1513, 1408, 1327, 1262, 1096, 934 cm⁻¹. Analysis calculated for $C_{180}H_{207}Gd_6N_{39}Na_{12}O_{71}S_7 \cdot 24H_2O$: C, 36.46; H, 4.33; N, 9.21; S, 3.78; found: C, 36.33; H, 4.07; N, 9.06; S 3.17.

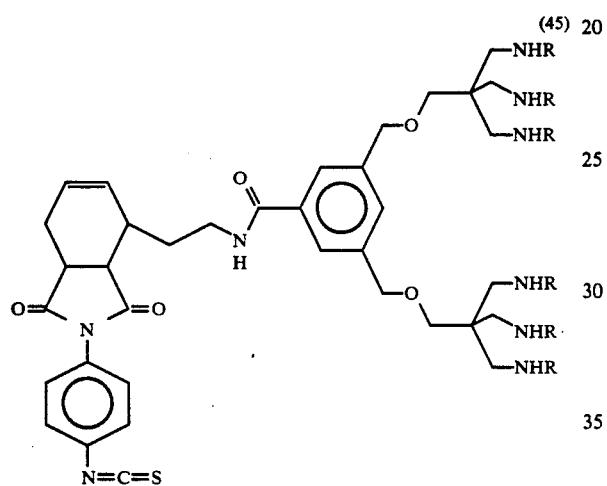
(45)

wherein R is

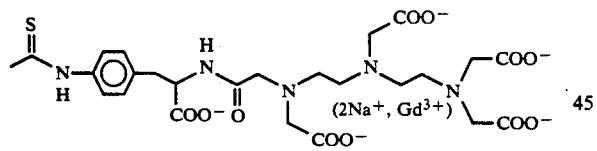

Although the above synthesis was demonstrated using chelate 42, it is clear that any chelate having a free isothiocyanate group can be linked to the primary amines on hexaamine 17 via similar thiourea-linkage chemistry. For MRI purposes, such other chelates would include chelates of paramagnetic metal ions other than $Gd^{3+}$, as well as other $Gd^{3+}$ chelates. Further, because of the wide utility of the above-described thiourea-linkage reaction involving primary amines (such as the amines on the several amplifier molecules of the present invention) and isothiocyanate moieties on molecules to be linked thereto, virtually any group having pharmacologic utility and an isothiocyanate moiety can be linked to an amplifier molecule of the present invention via the above-described chemistry. Such linkable groups include various chelators, fluorophores, radioactively tagged groups, electron-dense moieties, chemotherapeutic agents, toxins, boron-cage molecules, and various stable nitroxides.

I. Attachment of Nitroxide Paramagnetic Centers to a Phosphine Triamine

The following synthesis pathway is a method for attaching nitroxide paramagnetic groups to an existing triamine amplifier molecule (having an amplification factor of three) derived from phosphine.

N,N′-carbonyldiimidazole (130 mg, 0.80 mmol) was added to a stirred solution of nitroxide carboxylic acid 46 (149 mg, 0.80 mmol) in 3 mL dry THF. Nitroxide carboxylic acid 46 is described in Hideg and Lex, *J. Chem. Soc. Perkin Trans. I*, p. 1117 (1987). After 1 h at 25° C., a solution of triamine 47 (61 mg, 0.2 mmol) in 2 mL THF was added. Triamine 47 is described in Bartlett et al., *J. Am. Chem. Soc.* 100:5085 (1978). The solution was stirred for 24 h at 25° C. The solvent was removed and the residue was dissolved in CHCl₃ and washed with 1N HCl, followed by saturated aqueous NaHCO₃, then water. The organic phase was dried (MgSO₄) and evaporated to give crude 4,4′,4″-phosphinidyne-tri-[2,2,5-trimethyltetrahydropyrrol-1-oxy-5-(methylenecarbonyl)benzylamine](compound 48) (141 mg, 94% yield) as a yellow solid. A 50-mg sample was chromatographed over 1 g silica gel. The yellow band was eluted with 95:5 CH₂Cl₂:MeOH. The solvent was evaporated and the residue dried to give pure 49 (43 mg, 86% yield) as a yellow powder: mp 82°–83° C. (dec); IR 1663 cm⁻¹. Analysis calculated for $C_{48}H_{66}N_6O_6P$: C, 67.49; H, 7.79; N, 9.84; found: C, 67.35; H, 8.04; N, 9.55.

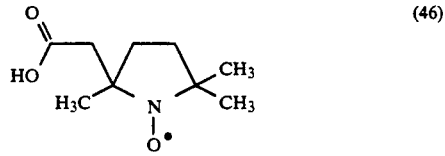
(46)

(47)

wherein R is

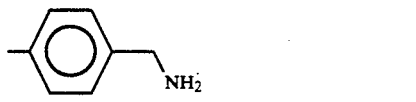

(48)

wherein R is

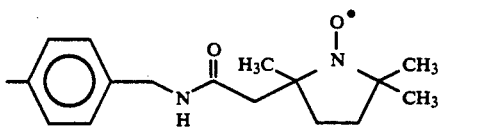

The above-described synthesis of compound 48 illustrated how one may attach several paramagnetic centers to an amine such as triamine 47; in this case, the paramagnetic centers are derived from the pyrrolidine nitroxide acid 46. Because the N,N′-carbonyldiimidizone method of acylation works smoothly for a wide variety of carboxylic acids and amines, other stable nitroxides having a terminal carboxylic acid group may be added to triamine 47 in a similar manner. In fact, this synthesis utilizing N,N'-carbonyldiimidizone may be used to attach a wide variety of pharmacologically useful groups to triamine 47 as well as the other amine amplifiers described above, so long as such groups have a terminal carboxylic acid moiety available for the acylation reaction.

Compound 48 can be used as a multiple paramagnetic center-containing contrast enhancing agent without attaching it to a targeting molecule. Alternatively, one may wish to attach compound 48 to a targeting molecule using chemistry appropriate to this new combination of functionality. Compound 48 is particularly useful because it contains a nucleophilic phosphine group which can effect a nucleophilic attack on a number of substrates.

It is also possible to introduce a 1,3-hexadiene moiety into molecules such as compound 48. Several examples of new synthesis pathways therefor are as follows, which begin with the synthesis of (E)-hexa-1,3,-dienyl bromoacetate: A mixture of (E)-3,5-hexadien-1-ol (192 mg, 1.96 mmol), bromoacetic acid (300 mg, 2.16 mmol), N,N'-dicyclohexylcarbodiimide (485 mg, 2.35 mmol), and 4-pyrrolidinopyridine (28 mg, 0.189 mmol) was stirred in 25 mL CH$_2$Cl$_2$ at 25° C. for 20 h. The mixture was filtered and the filtrate was evaporated to dryness. (E)-3,5-hexadien-1-ol is described in Stevens et al., *J. Am. Chem. Soc.* 98:6317 (1976) and Howden et al., *J. Am. Chem. Soc.* 88:1732 (1966). The residue was triturated with ether and the ether solution was evaporated to dryness. The residue was chromatographed over 5 g silica gel. Elution with CH$_2$Cl$_2$ gave (E)-hexa-1,3-dienyl bromoacetate (compound 49) (390 mg, 91% yield) as a colorless oil: IR 1737 cm$^{-1}$, NMR d 2.46 (q, 2), 3.83 (s, 2), 4.22 (t, 2), 5.03 (d, 1), 5.15 (d, 1), 5.60–5.72 (m, 1), 6.09–6.40 (m, 2). Analysis calculated for C$_8$H$_{11}$BrO$_2$: C, 43.84; H, 5.06; Br, 36.49; found: C, 43.72; H, 5.24; Br, 36.84.

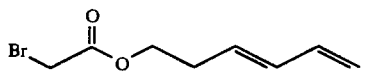

(49)

To demonstrate the validity of introducing a 1,3 diene moiety into molecules such as compound 48, a "test" synthesis was performed as follows: A solution of diene ester 49 (123 mg, 6.44 mmol) and triphenylphosphine (169 mg, 6.44 mmol) in 4 mL ether was refluxed for 40 h. Triphenylphosphine is a strong nucleophile that readily attaches at the halogen of compound 49 under mild conditions. The resulting white needles were isolated, washed with ether, and dried to give (3-oxa-nona-6,8-dienyl-2-one-1-yl)triphenylphosphonium bromide (compound 50) (260 mg, 96% yield) as white needles: mp 130°–133° C. (dec): IR 1733 cm$^{-1}$; NMR δ 2.25 (q, 2); 4.03 (t, 2), 5 02 (d, 1), 5.10 (d, 1), 5.38–5.48 (m, 1), 5.66 (dd, 2), 5.92–6.30 (m, 2), 7.60–7.95 (m, 15). Analysis calculated for C$_{26}$H$_{26}$BrO$_2$P: C, 64.85; H, 5.45; Br, 16.61; found: C, 64.47; H, 5.32; Br, 16.54.

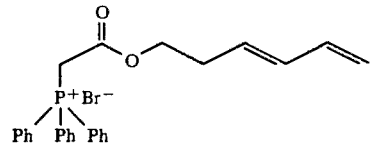

(50)

A solution of diene ester 49 (52.2 mg, 0.238 mmol) and N-(4-isothiocyanatophenyl)maleimide (compound 25) (55.0 mg, 0.238 mmol) in 2.5 mL dry CH$_3$CN was heated at 50°–55° C. for 17 h. The solvent was removed and the residue was chromatographed over 1 g silica gel. Elution with CH$_2$Cl$_2$ gave the Diels-Alder adduct 51 (97 mg, 91% yield) as a viscous yellow oil: IR 2100, 1729, 1713 cm$^{-1}$; NMR δ 2.15–2.65 (m, 4), 2.83 (dd, 1), 3.31–3.35 (m, 2), 3.85 (s, 2), 4.30–4.40 (m, 1), 4.45–4.55 (m, 1), 5.85 (dt, 1), 5.95–6.10 (m, 1), 7.27 (AA'BB', 4). Analysis calculated for C$_{19}$H$_{17}$BrN$_2$O$_4$S: C, 50.78; H, 3.82; N, 6.24; Br, 17.80; found: C, 50.98; H, 3.80; N, 6.24; Br, 18.00.

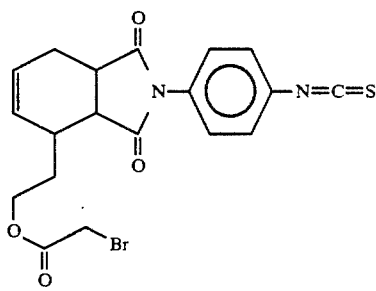

(51)

As discussed above, the Diels-Alder addition is so versatile that a number of different Diels-Alder adduct derivatives of compound 50 are possible, depending upon which dienophile is utilized. Compound 51 is a representative example of such an adduct. The above synthesis also shows that the isothiocyanate moiety is unaffected by the Diels-Alder reaction.

Two alternative synthetic pathways were used to synthesize a diamagnetic triphenyphosphine Diels-Alder adduct 52, one starting with the triphenylphosphonium bromide 50 and the other with the bromoacetate 51. In the first pathway, a solution of the triphenylphosphoniu-m-salt 50 (14.34 mg, 0.0298 mmol) and N-(4-isothiocyanatophenyl)maleimide (compound 25) (6.85 mg, 0.0298 mmol) in 0.4 mL CD$_3$CN was heated in an NMR tube at 40°–45° C. for 42 h, after which time the NMR spectrum indicated that the reaction was complete. Evaporation of the solvent gave compound 52 (21.2 mg, 100% yield) as a pale yellow solid. Again, the isothiocyanate moiety on compound 25 was not disturbed by the Diels-Alder reaction of compound 25 with the triphenylphosphonium salt 50.

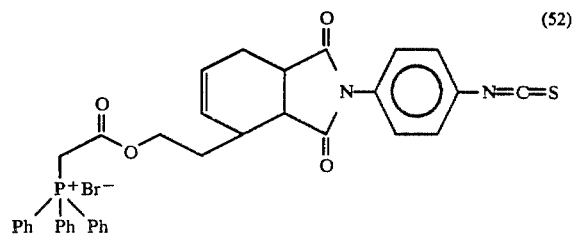

(52)

In the second pathway, a solution of the bromoacetate 51 (11.50 mg, 0.0256 mmol) and triphenylphosphine (6.70 mg, 0.0256 mmol) in dry 1.0 mL CH₃CN was heated at 40°-45° C. for 3 h (monitored by TLC). The solvent was removed and the residue was washed with ether and dried to give the diamagnetic triphenylphosphine Diels-Alder adduct 52 (17.1 mg, 94% yield) as a pale yellow powder: mp 114°-115° C. (dec); IR 2254, 2194, 2110, 2103, 1708, 1602, 1508, 1440, 1386, 1311, 1288, 1266, 1189, 1168, 1112, 978, 929 cm$^{-1}$; NMR (CD₃CN) δ 1.75-2.40 (m, 4), 2.60 (dd, 1), 3.10-3.35 (m, 2), 4.10-4.20 (m, 1), 4.22-4.35 (m, 1), 5.00 (dd, 2), 5.65-5.75 (m, 1), 5.90-6.00 (m, 1), 7.28 (AA'BB', 4), 7.60-8.00 (m, 15). Analysis calculated for C₃₇H₃₂BrN₂O₄PS.H₂O: C, 60.90; H, 4.70; N, 3.84; found: C, 60.94; H, 4.45; N, 4.14. This alternative pathway shows that the Diels-Alder reaction can be performed first, yielding the bromoacetate 51, which can be reacted with triphenylphosphine to yield the triphenylphosphine Diels-Alder adduct 52. Again, the isothiocyanate moiety is maintained intact during the Diels-Alder reaction.

After the above "test" reactions using diamagnetic analogs were completed, a bifunctional nitroxide amplifier derived from triphenylphosphine and including an isothiocyanate moiety was successfully synthesized as follows: A solution of bromoacetate 51 (12.5 mg, 0.0278 mmol) and nitroxide phosphine 48 (23.7 mg, 0 0278 mmol) in 0.95 mL dry CH₃CN was heated at 40°-45° C. for 4 h (monitored by TLC). The solvent was removed and the residue was washed with ether and dried to give the nitroxide phosphonium salt 53 (34 mg, 94% yield) as a yellow powder: mp 225°-230° C. (dec), IR 2977, 2935, 2250, 2111, 2102, 1732, 1708, 1666, 1602, 1530, 1509, 1463, 1408, 1380, 1365, 1315, 1286, 1255, 1189, 1171, 1112 cm$^{-1}$. Analysis calculated for C₆₇H₈₃BrN₈O₁₀PS.3H₂O: C, 59.27; H, 6.61; N, 8.26; found: C, 58.92; H, 6.55; N, 8.14.

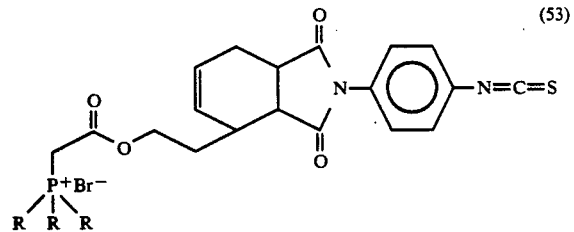

(53)

wherein R is

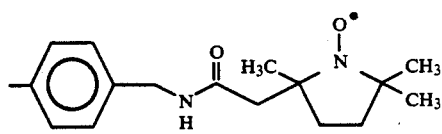

In compound 53, the R group need not be the pyrrolidine nitroxide as shown. It may also be any of a number of other stable nitroxides. It is also possible to incorporate, for example, the gadolinium complexing group shown in compounds 43, 44 and 45. The isothiocyanate group enables compound 53 to be attached to biomolecules at specific sites.

J. Synthesis of Various Four- and Six-Branched Amplifier Molecules From (E)-Hexa-3,5-dienyl-3,5-bis-(bromomethyl) benzoate (E)-hexa-3,5-dienyl-3,5-bis-(bromomethyl)benzoate (compound 54) has been found to be a useful starting compound for synthesizing a variety of amplifier molecules using chemistry similar to that discussed supra. For example, a solution of (E)-3,5-hexadien-1-ol (50 mg, 0.510 mmol), 3,5-bis-(bromomethyl)benzoic acid (compound 1) (157 mg, 0.51 mmol), N,N'-dicyclohexylcarbodiimide (116 mg, 0.561 mmol), and 4-pyrrolidinopyridine (8 mg, 0.054 mmol) in 5 mL CH₂Cl₂ was stirred at 25° C. for 20 h and then filtered. The filtrate was concentrated to 1 mL and then chromatographed over 2 g silica gel. Elution with CH₂Cl₂ gave the dibromide 54 (139 mg, 70% yield) as a white solid: mp 50°-52° C.; IR 1719 cm$^{-1}$; NMR δ 2.56 (q, 2), 4.38 (t, 2), 4.50 (s, 4), 5.03 (d, 1), 5.16 (d, 1), 5.68-5.80 (m, 1), 6.15-6.42 (m, 2), 7.62 (s, 1), 7.98 (s, 2). Analysis calculated for C₁₅H₁₆Br₂O₂: C, 46.40; H, 4.16; found: C, 46.14; H, 4.15.

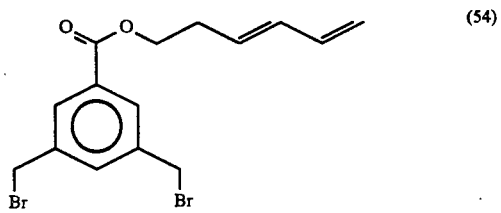

(54)

Since there are two benzylic bromine atoms in compound 54 that can be displaced by the strongly nucleophilic phosphorus atom in phosphine, it is possible by combining compound 54 with phosphine derivatives to synthesize amplifier molecules having twice the capacity for paramagnetic centers over that of, for example, compound 53. For purposes of establishing the correctness of the envisaged chemistry, compound 54 was reacted with triphenylphosphine according to the following: A solution of the dibromide 54 (23.10 mg, 0.0595 mmol) and triphenylphosphine (31.2 mg, 0.119 mmol) in 1.0 mL dry CH₃CN was heated at 40°-45° C. for 24 h and the solvent was evaporated. The residue was washed with ether and dried to give the bisphosphonium salt 55 (52 mg, 96% yield) as a pale yellow powder: mp 140°-141° C. (dec); IR 1719 cm$^{-1}$; NMR (CD₃CN) δ 2.34 (q, 2), 4.10 (t, 2), 4.95 (d, 4), 5.02 (d, 1), 5.13 (d, 1), 5.58-5.72 (m, 1), 6.05-6.40 (m, 2), 7.30-7.90 (m, 33). Analysis calculated for C₅₁H₄₆Br₂O₂P₂.2H₂O: C, 64.55; H, 5.32. Found: C, 64.67; H, 4.99. This reaction established that both bromine atoms are displaceable.

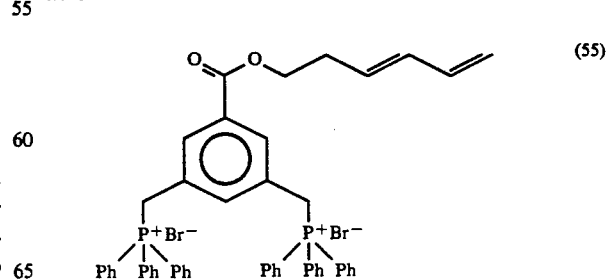

(55)

Next, the hexadiene of compound 54 was made to undergo a Diels-Alder reaction with N-(4-isothiocyanatophenyl)maleimide, as an example of an appropriate isothiocyanate-containing dienophile, to yield an isothiocyanate, as follows: A solution of diene ester 54 (42 mg, 0.108 mmol) and N-(4-isothiocyanatophenyl)-maleimide (compound 25) (25 mg, 0.108 mmol) in 1.5 mL dry CH₃CN was heated at 60°-65° C. for 48 h. Afterward, the solvent was removed. The residue was chromatographed over 1 g silica gel. Elution with CH₂Cl₂ gave the Diels-Alder adduct 56 (59 mg, 88% yield) as a yellow viscous oil: IR 2100, 1712 cm$^{-1}$; NMR δ 2.10-2.65 (m, 4), 2.83 (dd, 1), 3.25-3.45 (m, 2), 4.50 (s, 4), 4.50-4.70 (m, 2), 5.85-5.95 (m, 1), 6.00-6.10 (m, 1), 7.24 (AA'BB', 4), 7.62 (2, 1), 7.99 (s, 2). Analysis calculated for $C_{26}H_{22}Br_2N_2O_4S$: C, 50.49; H, 3.59; N, 4.53; found: C, 50.75; H, 3.49; N, 4.40.

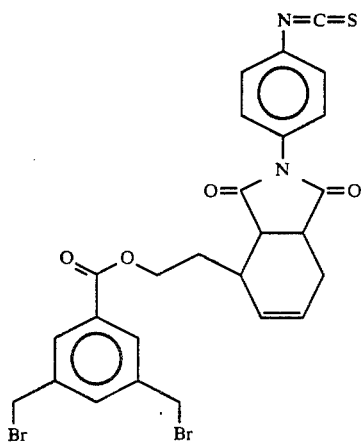

In a confirmatory experiment, isothiocyanate 56 was reacted with triphenylphosphine to yield a diamagnetic salt suitable for analysis, as follows: A solution of dibromide 56 (6.9 mg, 0.0111 mmol) and triphenylphosphine (5.82 mg, 0.0222 mmol) in dry 1.0 mL CH₃CN was heated at 40°—45° C. for 4 h (monitored by TLC). Afterward, the solvent was removed. The residue was washed with ether and dried to yield bisphosphonium salt 57 (11 mg, 86% yield) as a pale yellow solid: mp 185°-187° C. (dec); IR 2255, 2195, 2114, 1708, 1508, 1440, 1384, 1310, 1220, 1188, 1139, 1112 cm$^{-1}$; NMR (CD₃CN) δ 2.10-2.70 (m, 4), 3.35-3.50 (m, 2); 4.10-4.24 (m, 1), 4.25-4.35 (m, 1), 4.80-5.20 (m, 1) 5.04 (d, 2), 5.09 (d, 2), 5.75-5.90 (m, 1), 5.90-6.10 (m, 1), 7.20-7.90 (m, 37). Analysis calculated for $C_{62}H_{52}Br_2N_2O_4P_2S·H_2O$: C, 64.13; H, 4.69; N, 2.41; found: C, 64.40; H, 4.58; N, 2.31.

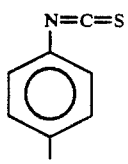

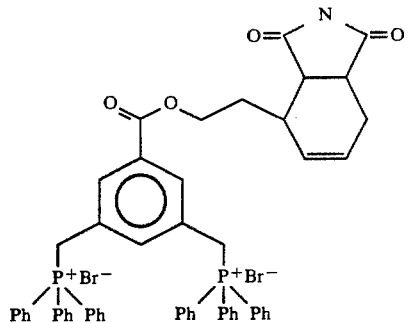

Finally, isothiocyanate 56 was reacted with nitroxide phosphine 48 in an alkylation reaction on phosphorus, as follows: A solution of compound 56 (7.2 mg, 0.0116 mmol) and compound 48 (19.8 mg, 0.0232 mmol) in 1.0 mL dry CH₃CN was heated at 40°-45° C. for 4 h (monitored by TLC). Afterward, the solvent was removed. The residue was washed with ether and dried to give the nitroxide bisphosphonium salt 58 (22.8 mg, 84% yield) as a pale yellow solid: mp >250° C.; IR 2977, 2935, 2876, 2254, 2115, 2107, 2100, 2097, 1708, 1666, 1602, 1563, 1531, 1509, 1462, 1434, 1408, 1380, 1372, 1365, 1315, 1253, 1219, 1170, 1112 cm$^{-1}$. Analysis calculated for $C_{122}H_{154}Br_2N_{14}O_{16}P_2S·3H_2O$: C, 61.54; H, 6.78; N, 8.24; found: C, 61.61: H, 6.70: N, 8.02.

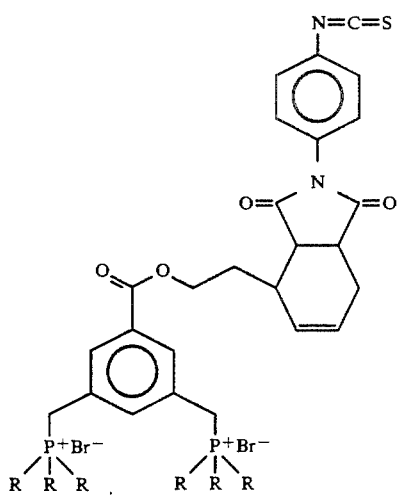

wherein R is

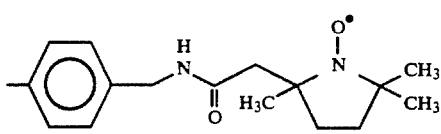

Compound 58 is a bifunctional paramagnetic spin-relaxer molecule with six pyrrolidine nitroxide groups and an isothiocyanate tail useful attaching the compound via thiourea linkages to biomolecules. Alternatively, derivatives of compound 58 lacking the isothiocyanate moiety can be used if attachment to a target is not required or desired. Note also that the paramagnetic centers on compound 58 need not be nitroxide. For example, one could have acylated triamine 47 with isothiocyanate 38 or 42. As a further alternative, any of the wide variety of possible variations of the phosphine compound 48 (see above discussion of compound 48) could have been reacted with isothiocyanate 56 in the same manner as was compound 48.

Dibromide 54 can also be converted into an amplifier molecule having an amplification factor of two via the following synthesis reactions:

A solution of the dibromide 54 (75 mg, 0.193 mmol) and NaN$_3$ (150 mg, 2.31 mmol) in 8 mL of 10:1 acetone:water was refluxed for 4 h. Afterward, the solvent was removed. The residue was dissolved in CH$_2$Cl$_2$ and dried (MgSO$_4$). Evaporation of the solvent gave (E)-hexa-3,5-dienyl 3,5-bis-(azidomethyl)benzoate (compound 59) (59 mg, 98% yield) as an oil suitable for the next reaction: IR 2103, 1719 cm$^{-1}$; NMR δ 2.56 (q, 2), 4.38 (t, 2), 4.43 (s, 4), 5.03 (d, 1), 5.15 (d, 1), 5.68–5.80 (m, 1), 6.15–6.40 (m, 2), 7.48 (s, 1), 7.95 (s, 2).

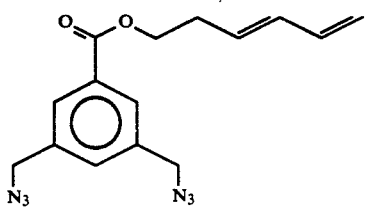
(59)

A solution of the diazide 59 (47 mg, 0.15 mmol) and triphenylphosphine (83 mg 0.32 mmol) in 5 mL dry ether was refluxed for 3 h. Afterward, the solvent was removed and the residue was dried, giving the waxy phosphinimine derivative (115 mg, 98% yield; IR showed no azide absorption). This material was dissolved in 5 mL of 1:1 EtOH:water and stirred at 25° C. for 20 h. Afterward, the solvent was removed. The residue was treated with 4 mL water and the mixture was acidified at 0° C. to pH 2 using 2 N HCl. Triphenylphosphine oxide was removed by extraction with CH$_2$Cl$_2$. The aqueous solution was basified at 0° C. to pH 14 by the addition of 10% NaOH and then saturated with NaCl. The diamine was extracted into CH$_2$Cl$_2$. The extract was dried (K$_2$CO$_3$) and evaporated to give the amplifier (E)-hexa-3,5-dienyl 3,5-bis-(aminomethyl)-benzoate (compound 60) (28 mg, 73% yield) as a colorless oil. The diamine 60 can participate in any of the above-described reactions effecting the attachment of pharmacologically active groups to the primary amines and, if desired, the conversion into a bifunctional form via the Diels-Alder reaction.

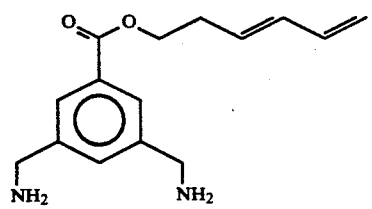
(60)

To facilitate analysis of diamine 60, the compound was converted to its tosylate salt according to the following: A 14-mg (0.054 mmol) sample of diamine 60 was dissolved in 0.3 mL EtOH and treated with a solution of p-toluenesulfonic acid monohydrate (20.5 mg, 0.108 mmol) in 0.3 mL EtOH. The solution was allowed to stand at 4° C. overnight. Filtration and drying gave the tosylate salt 61 (15 mg, 49% yield) as white needles: mp 215°–218° C. (dec); NMR (D$_2$O) δ 2.36 (s, 6), 2.57 (q, 2), 4.25 (s, 4), 4.43 (t, 2), 5.01 (d, 1), 5.14 (d, 1), 5.75–5.90 (m, 1), 6.15–6.45 (m, 2), 7.49 (AA'BB', 8), 7.71 (s, 1), 8.09 (s, 2). Analysis calculated for C$_{29}$H$_{36}$N$_2$O$_8$S$_2$: C, 57.60; H, 6.00; N, 4.64; found: C, 57.88; H, 6.04; N, 4.86.

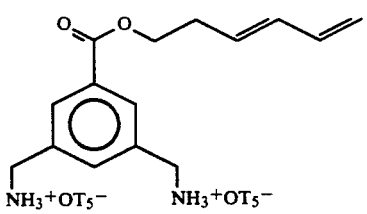
(61)

K. Synthesis of Alternative Gadolinium and Bismuth Complexing Agents from DTPA The following is a description of an alternative method for attaching an isothiocyanate group onto diethylenetriaminepentaacetic acid (DTPA) in order to convert the latter into a bifunctional molecule. In this work, DTPA (Aldrich), EDTA (ethylene-diaminepentaacetic acid, Sigma), and GdCl$_3$ (Aldrich) were used without further purification. Diisopropylamine (Aldrich), HMPA (hexamethylphosphoric triamide, Aldrich), benzyl bromide (Aldrich), and thionyl chloride (J. T. Baker) were all purified by standard methods prior to use. The compound n-butyllithium was purchased from Aldrich as a 2.5M solution in hexanes. Anhydrous THF (tetrahydrofuran) was obtained by distillation under N$_2$ from sodium benzophenone ketal. LDA (lithium diisopropylamide) was prepared fresh for each reaction. Proton NMR spectra were obtained using a G.E. QE 300 instrument. The samples were dissolved in CDCl$_3$ (7.26 ppm), CD$_3$OD (3.30 pm) or D$_2$O (4.80 ppm) and the chemical shifts reported in ppm on the δ scale using the residual proton absorbances of these solvents as references. Infrared spectra were obtained as KBr pellets on a Nicolet 5DXB FTIR spectrometer. Flash chromatography was performed on Davisil ™ grade 643 silica gel (mesh 200–425, Aldrich). Preparative thin-layer chromatography was performed on Whatman 1000 µ silica gel plates. All reactions were performed under a dry N$_2$ atmosphere unless otherwise stated.

DTPA (compound 31, 7.60 g 19.3 mmol) was suspended and stirred in 35 mL dry MeOH while cooled in an ice/H$_2$O bath as SOCl$_2$ (23.0 g, 193.2 mmol) was added slowly dropwise. The resulting clear solution was stirred for 6 h, followed by stripping off the MeOH by rotary evaporation. The residue, a white solid, was suspended in 35 mL Et$_2$O and cooled in an ice/H$_2$O bath as 50 mL saturated aqueous NaHCO$_3$ was slowly added. The organic layer was removed and the aqueous layer was extracted three times with 75 mL Et$_2$O. The extracts were combined, dried (Na$_2$SO$_4$), evaporated to dryness, then maintained for 12h at 0.1 mm Hg and 25° C., yielding the DTPA pentamethyl ester (compound 32) (6.61 g, 73% yield), as a very pale yellow oil. NMR(CDCl$_3$) δ 2.76–2.82 (m, 8), 3.47–3.70 (m, 25). Analysis calculated for C$_{19}$H$_{33}$N$_3$O$_{10}$.H$_2$O: C, 47.39; H, 7.33; N, 8.72; found: C, 47.24; H, 6.94; N, 8.52.

Pentamethyl ester 32 (4.97 g, 10.60 mmol) was dried for 18 h at 25° C. and at 0.05 mm Hg vacuum prior to use giving 4.92 g (10.5 mmol) of a very pale yellow oil. The oil was dissolved in 30 mL anhydrous THF. LDA was prepared by dissolving diisopropylamine (1.1 g, 10.5 mmol) in 15 mL anhydrous THF at −78° C. and adding n-butyllithium (4.2 mL, 10.5 mmol), followed by stirring for 15 min. The ester/THF solution was added to the LDA solution via cannula over 10 min and then stirred an additional 20 min. Twenty mL of a THF solution of benzyl bromide (2.1 g, 12.6 mmol) and HMPA (0.6 g, 3.1 mmol) were added via cannula over 30 min to the pale yellow solution. Then, the mixture was stirred for 12 h, during which time it slowly warmed to 25° C. The resulting yellow suspension was added to 15 mL cracked ice/H$_2$O and the organic layer was removed. The aqueous layer was extracted three times with 50 mL ethyl acetate. The organic layers were combined, dried (K$_2$CO$_3$) and evaporated to dryness, yielding a yellow oil (5.0 g). Flash chromatography over 30 g silica gel, eluted with 3:1 ET$_2$O:THF gave benzyldiethylenetriaminepentaacetic acid pentamethyl ester (compound 62) (1.45 g, 25% yield) as a pale yellow oil. An analytical sample was prepared by preparative TLC eluted with 3:1 ET$_2$O:THF giving a pale yellow oil. NMR(CDCl$_3$) δ 2.64–2.91 (m, 9), 3.39–3.60 (m, 10), 3.63–3.66 (m, 15), 7.15–7.23 (m, 5). Analysis calculated for C$_{26}$H$_{39}$N$_3$.5H$_2$O: C, 53.80; H, 7.29; N, 7.24; found: C, 53.92; H, 7.04; N, 7.35.

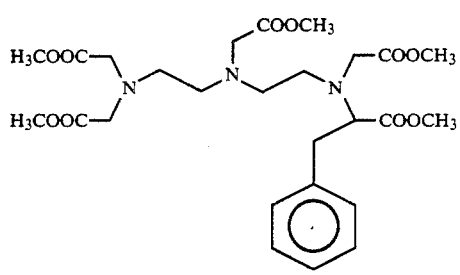

(62)

The benzylated pentamethyl ester 62, (1.45 g, 2.6 mmol) was dissolved into 5 mL of 97% sulfuric acid and stirred at 3° C. Concentrated HNO$_3$ (200 μL, 3.2 mmol) was to this stirred yellow solution. The solution was stirred for 3 h, during which time it returned to 25° C. The mixture was poured into 3 mL cracked ice/H$_2$/O and taken to pH 5 with 7N NaOH, then evaporated to dryness. The yellow residue was suspended in MeOH and evaporated (3×10 mL) to remove most of the water. The residue was again suspended in 10 mL MeOH and cooled in an ice bath, while SOCl$_2$ (4.6 g, 39.0 mmol) was added slowly. This yellow solution was stirred for 14 h, then the MeOH was stripped off via rotary evaporation. The residue was suspended in 150 mL Et$_2$O, cooled in an ice bath, and followed by slow addition of 35 mL saturated aqueous NaHCO$_3$. This solution was transferred to a separatory funnel and the organic layer removed. The aqueous layer was extracted three times with 100 mL Et$_2$O. The organic layers were combined, dried (K$_2$CO$_3$), and evaporated to dryness giving a dark yellow oil (1.30 g). Flash chromatography over 10 g silica gel, eluted with 3:1 ET$_2$O:THF gave (4-nitrobenzyl)ethylenediaminepentaacetic acid pentamethyl ester (compound 63) (1.25 g, 81% yield) as a yellow oil. NMR δ 2.61–2.91 (m, 8), 3.0–3.21 (m, 2), 3.55–3.70 (m, 24), 7.45 (d, 2), 8.16 (d, 2). Analysis calculated for C$_{26}$H$_{38}$N$_4$O$_{12}$: C, 52.17; H, 6.37; N, 9.36; found C, 52.09; H, 6.40, N, 9.11.

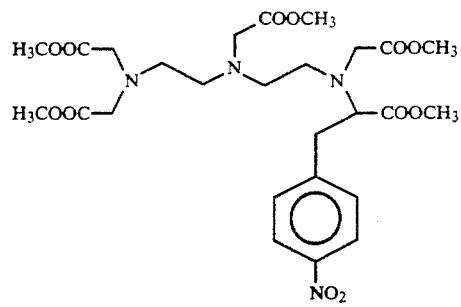

(63)

4-Nitrobenzyl pentamethyl ester 63 (306.2 mg, 0.5 mmol) was dissolved in 20 mL methanol in a Parr shaker bottle. Then, 30% Pd/C (palladium on carbon catalyst) (47.2 mg) was added. The suspension was shaken for 3 h under a 60 psi hydrogen atmosphere. At the end of this time, TLC showed complete conversion of the nitro compound to the aromatic amine (4-aminobenzyl)diethylenetriaminepentaacetic acid pentamethyl ester (compound 64). The suspension was filtered through Celite and the colorless solution used without further purification or concentration.

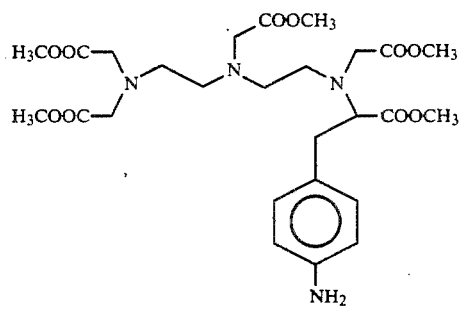

(64)

The methanolic solution of the amine 64 was transferred to a 100 mL round-bottomed flask equipped with a magnetic stirrer and a solution of LiOH (105 mg, 2.5 mmol) in 2 mL H$_2$O was added. After this addition, the colorless solution of the amine ester became a pale yellow color. The solution was stirred for 3 h, then evaporated to dryness. The residue was suspended in MeOH and evaporated (3×10 mL) to remove most of the water. The resulting pale yellow powder, (4-aminobenzyl)-diethylenetriaminepentaacetic acid pentalithium salt (compound 65), was pure by NMR. NMR (CD$_3$OD) δ2.25–2.80 (m, 9), 3.10–3.15 (m, 2 , 3.41–3.50 (m, 8), 6.61 (d, 2), 7.03 (d, 2).

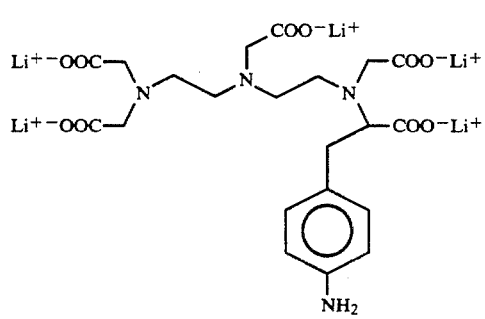

(65)

A 5 mL methanolic solution of amino pentalithium salt 65 (0.33 mmol), was treated with a 0.12N solution of thiophosgene in methanol (1.7 mL, 0.3 mmol) and stirred for 1 h. The mixture was spotted onto a TLC plate and tested with Ehrlich's reagent which showed that all of the aromatic amine had been consumed. The solution was evaporated to dryness giving 215.0 mg of a very pale yellow powder, (4-isothiocyanatobenzyl)-diethylenetriaminepentaacetic acid pentalithium salt (compound 66) NMR(D$_2$O) $\delta$ 2.98-3.32 (m, 17), 3.53-3.60 (m, 2), 7.10 (d, 2), 7.30 (d, 2). Analysis calculated for C$_{22}$H$_{25}$N$_4$O$_{10}$S$_1$Li$_3$. 2LiCl.H$_2$O: C, 41.50; H, 4.75; N, 8.75; found: C, 41.47; H, 4.75; N, 8.80.

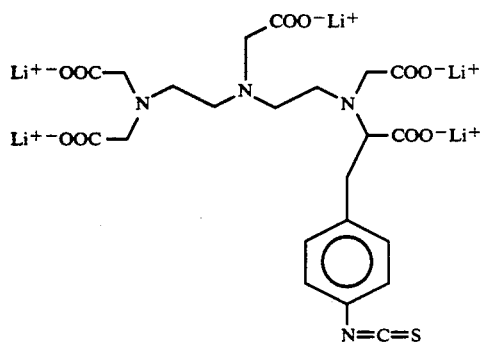

(66)

Isothiocyanate ligand 66 (30.3 mg, 5.3×10$^{-2}$ mmol) was dissolved in 10 mL methanol with stirring. BiCl$_3$ (5.3×10$^{-2}$ mmol) from a methanolic standard solution was added. The solution was stirred for 0.25 h, followed by addition of NaOH (1.0×10$^{-1}$ mmol) from a standard methanolic solution. The solution was stirred an additional 0.5 h, then evaporated to dryness. The white residue was taken up into 2 mL MeOH and precipitated by the addition of 25 mL dry acetone. The solid was isolated by centrifugation, washed with acetone (3×10 mL), dissolved into 5 mL H$_2$O, filtered through a cotton plug, and lyophilized. A white powder, bismuth-(III)-(4-isothiocyanatobenzyl)diethylenetriaminepentaacetic acid[2Na+] (compound 67) (37.7 mg, 90% yield) was isolated. Analysis calculated for C$_{22}$H$_{23}$N$_4$O$_{10}$S$_1$Bi$_1$Na$_2$.H$_2$O: C, 30.63; H, 3.62; N, 6.49; found: C, 30.77; H, 3.29; N, 6.51.

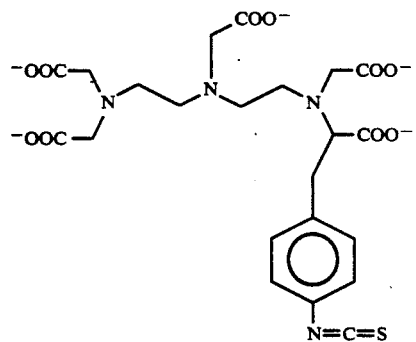

(67)

A 5 mL methanolic solution of isothiocyanate ligand 66 (200 mg, 0.30 mmol) was treated with 5 mL of a methanolic solution of GdCl: (122.7 mg, 0.30 mmol) with stirring. The metal/ligand solution was treated with NaOH (0.6 mmol) from a methanolic standard solution, stirred for 0.5 h, then evaporated to dryness. The residue was resuspended in 2 mL dry methanol and a pale yellow solid precipitated by the addition of 25 mL dry acetone. The solid was isolated by centrifugation, washed with dry acetone (3×10 mL), then dissolved in 10 mL water. The aqueous solution was filtered through a cotton plug, then lyophilized. The product was isolated as a white powder, gadolinium-(III)-(4-isothiocyanatobenzyl)diethylenetriaminepentaacetic acid[2Na+] (compound 68) (128.8 mg, 67% yield). Analysis calculated for C$_{22}$H$_{23}$N$_4$O$_{10}$S$_1$Gd$_1$Na$_2$8.5H$_2$O: C, 29.62; H, 4.52; N, 6.28; found: C, 29.62; H, 3.76; N, 5.77.

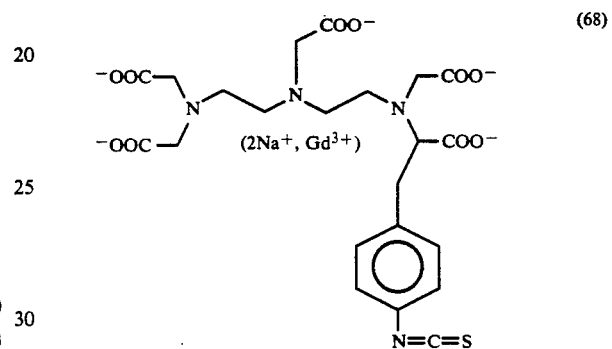

(68)

L. Synthesis of a Polylysine Derivative Bearing Multiple Gadolinium Chelators In this example, diagrammed in Schemes 1, 2 and 3, a derivative of polylysine was used as a substrate to react with a gadolinium chelate of DTPA isothiocyanate. Each molecule of the product of the reaction contained many gadolinium DTPA chelator groups. The product was then made bifunctional by acetylation, hydrogenation and isothiocyanation, which introduced an isothiocyanate moiety at one end of the molecule, rendering the molecule capable of conjugation with a protein molecule such as an immunoglobulin (antibody) molecule. Such a conjugate was another form of a targeting amplified molecule.

In the work described below, NMR spectra were obtained using a GE QE-300 instrument; the samples were dissolved in CDCl$_3$ unless otherwise stated. IR spectra were obtained on a Nicolet 5DXB spectrometer. UV spectra were obtained on a Beckman DU-7 spectrophotometer. Column chromatography was performed on Davisil TM grade silica gel (mesh 200-425, Aldrich). Preparative thin layer chromatography was performed on Whatman 100μ silica gel plates. Dialysis was performed using a cellulose membrane tubing, MW cutoff 12,000-14,000, VWR Scientific, Inc. Poly-E-CB2-dl-lysine was purchased from Sigma, MW 17,000-20,000.

a. Scheme 1 Reactions

Scheme 1 reactions are diagrammed as follows and described in detail below.

Scheme 1

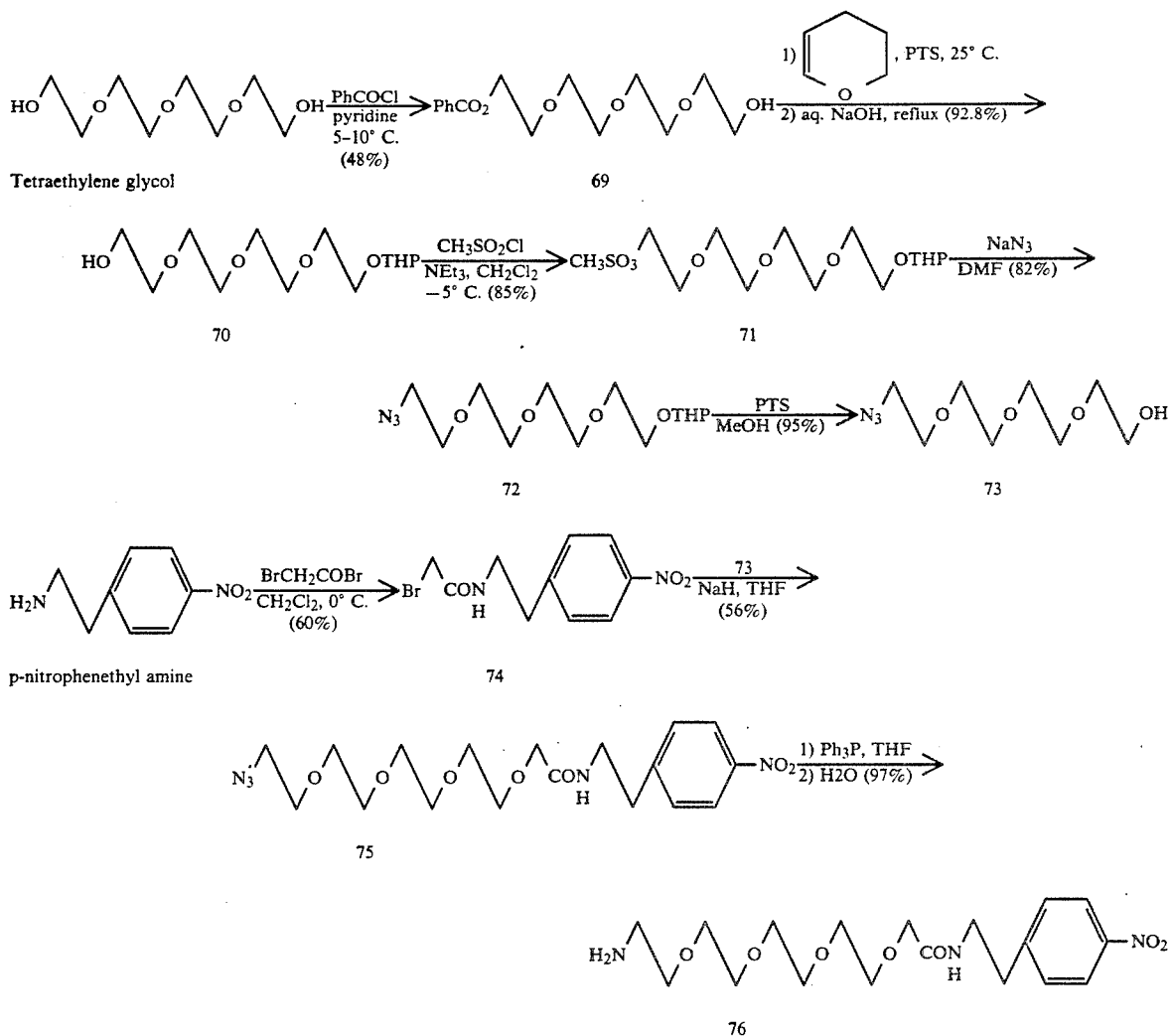

Tetraethylene glycol (19.4 g, 0.10 mol) in 40 mL pyridine was stirred at 10° C. Benzyl chloride (PhCOCl) (14.0 g, 0.10 mol) was added dropwise over 30 min. The resulting mixture was then stirred at 25° C. for 3 h and then poured onto 100 g cracked ice and extracted four times with 50 mL CHCl₃. The extracts were combined, washed with 80 mL of 6N HCl, then with 50 mL of saturated aqueous NaHCO₃. The extract was dried (MgSO₄) and the CHCl₃ removed by rotary evaporation. The resulting oil was chromatographed over 120 g silica gel; elution with 400 mL EtOAc gave 14.2 g (47.8% yield) of tetraethylene glycol monobenzoate (compound 69) as a colorless oil. IR (film) 3452, 3065, 1722, 1602, 1276, 1111, 714 cm$^{-1}$; NMR δ 3.58–3.70 (m, 12H), 3.84 (t, 2H), 4.47 (t, 2H), 7.41–7.46 (m, 2H), 7.54–7.58 (m, 1H), 8.05–8.08 (m, 2H) ppm.

Dihydropyran (4.6 g, 55 mmol) was added dropwise to a mixture of tetraethylene glycol monobenzoate 69 (14.9 g, 50 mmol) and 30 mg of p-toluenesulfonic (PTS) acid over 20 min at 25° C. with stirring. The reaction was complete after stirring 2 h (as determined by TLC, 10:1 CHCl₃:MeOH). To this reaction mixture was added a solution of NaOH (4.06 g, 100 mmol) in 25 mL H₂O and refluxed for 1 h. The resulting homogenous solution was extracted four times with 50 mL CHCl₃. The extract was dried (MgSO₄) and rotoevaporated, forming 12.9 g (92.8% yield) of mono-THP-ether of tetraethylene glycol (compound 70) as a colorless oil. NMR δ 1.51–1.85 (m, 6H), 3.47–3.53 (m, 2H), 3.60–3.72 (m, 2H), 3.83–3.90 (m, 2H), 4.62 (t, 1H) ppm.

Triethylamine (NEt₃) (6.50 g, 65 mmol) was added to a solution of the mono-THP-ether of tetraethylene glycol 70 (12.51 g, 45 mmol) in 200 mL CH₂Cl₂. The solution was cooled to −5° C. and methanesulfonyl chloride (7.50 g, 65 mmol) was added dropwise over 30 min. After stirring at 25° C. for 30 min, the reaction mixture was transferred to a separatory funnel, washed four times with 50 mL H₂O, dried (MgSO₄), and rotoevaporated to dryness. The residue was chromatographed over 80 g silica gel; elution with 6:1 hexane:EtOAc giving 13.6 g (85% yield) of 11-tetrahydropyranyloxy-3,6,9-trioxa-undecane-1-ol-methane-sulfonate (compound 71) as a yellow oil. NMR δ 1.51–1.82 (m, 6H), 3.08 (s, 3H), 3.45–3.90 (m, 16H), 4.38 (t, 2H), 4.62 (t, 1H) ppm.

A suspension of NaN₃ (14.72 g, 228 mmol) in 12 mL H₂O was added to a solution of the O-mesyl-O-tetrahydropyranyltetraethylene glycol 71 (13.33 g, 38 mmol) in 150 mL DMF. The reaction mixture was then stirred under N₂ at 100° C. for 3 h. The solvent was removed under reduced pressure and the semi-solid residue was washed four times with 50 mL ether. The ether solution was washed twice with 50 mL H₂O, then with 50 mL brine, dried (MgSO₄), and rotoevaporated giving 9.30 g (82% yield) of 1 azido-11-tetrahydropyranyloxy-3,6,9-trioxaundecane (compound 72) as a colorless Oil. IR (film) 2107, 1455, 1347, 1127 cm⁻¹; NMR δ 1.48-1.90 (m, 6H), 3.39 (t, 2H), 3.47-3.91 (m, 16H), 6.45 (t, 1H) ppm.

p-toluenesulfonic acid monohydrate (PTS) (447 mg, 2.35 mmol) was added to a solution of the azido THP ether 72 (9.09 g, 30 mmol) in 200 mL MeOH. The resulting mixture was stirred under N₂ at 25° C. for 3 h. At the end of this time, the methanol was removed by rotoevaporation. The residue was dissolved in 100 mL CHCl₃, washed three times with 50 mL saturated aqueous NaHCO₃, and then with 50 mL H₂O, dried (MgSO₄), and rotoevaporated to dryness, giving 6.30 g (96% yield) of 1-azido-3,6,9-trioxaundecan-11-ol (compound 73) as a colorless oil. IR (film) 3462, 2107, 1456, 1290, 1125 cm⁻¹; NMR δ 2.41 (t, 1H), 3.40 (t, 2H), 3.60-3.76 (m, 14H) ppm. Analysis calculated for $C_8H_{17}N_3O_4$: C, 43.82; H, 7.82; N, 19.17; found: C, 43.91; H, 7.94; N, 19.12.

Bromoacetyl bromide (806 mg, 4.0 mmol) was added dropwise to a solution of p-nitrophenylethylamine (665 mg, 4.0 mmol, freshly prepared from the hydrochloride salt) in 30 mL CH₂Cl₂ over 6 min at 0° C. with stirring. Then, the reaction mixture was stirred at 0° C. for 1 h. The resulting precipitate was filtered off and washed twice with 10 mL CH₂Cl₂, which was combined with tiltrate and rotoevaporated to dryness. Chromatography over 20 g silica gel and elution with 5:3 ethyl acetate:hexane gave crystalline N-(4-nitrophenylethyl)-bromoacetamide (compound 74). Recrystallization from ethyl acetate-hexane gave 290 mg (58% yield) of compound 74 as yellow needles: mp 123°-124° C. IR (nujol) 3276, 1659, 1515, 1343 cm⁻¹; NMR δ 2.99 (t, 2H), 3.60 (q, 2H), 3.88 (s, 2H), 6.54 (m, 1H), 7.38-8.20 (AA'BB', 4H) ppm.

To a solution of the azido alcohol 73 (220 mg, 1.0 mmol) in 10 mL dry THF was added sodium hydride (56 mg, 50%, 1.16 mmol). After stirring 15 min a solution of the bromoacetamide derivative 74 (290 mg, 1.0 mmol) in 5.0 mL dry THF was added dropwise at 5° C. over 15 min with stirring. The resulting mixture was stirred at 25° C. for 3 h, then rotoevaporated to dryness and chromatographed over silica gel. Elution with 20:1 CHCl₃:MeOH gave 235 mg (56% yield) of N-(4-nitrophenylethyl)-13-azido-2,5,8,11-tetraoxa-tetradecanamide (compound 75) as a pale yellow oil. IR (film) 3343, 2107, 1675, 1516, 1351, 1111 cm⁻¹; NMR δ 2.97 (t, 2H), 3.37 (t, 2H), 3.55-3.67 (m, 16H), 3.97 (s, 2H), 7.18-7.23 (m, 1H), 7.38-8.18 (AA'BB', 4H) ppm. Analysis calculated for $C_{18}H_{27}N_5O_7$: C, 50.18; H, 6.40; N, 16.47; found: C, 50.87; H, 6.49; N, 16.48.

Triphenylphosphine (Ph₃P) (410 mg, 1.56 mmol) was added to a solution of the azido compound 75 (480 mg, 1.06 mmol) in 26 mL dry THF. The mixture was refluxed for 90 min, then 3.0 mL H₂O was added and the resulting mixture was refluxed for 1 h. The reaction mixture was then rotoevaporated to dryness and the residue was dissolved in 20 mL CH₂Cl₂, acidified with 10 mL of 1N HCl and the organic phase was separated. The aqueous phase was washed twice with 5 mL CH₂Cl₂, basified with 4N NaOH to pH 10, then extracted with CH₂Cl₂. The extracts were combined and rotaevaporated to dryness, giving a yellow oil which was purified by preparative TLC (8.5:1.5:0.2 CHCl₃:MeOH:conc. NH₄OH) giving 439 mg (97% yield) of N-(4-nitrophenylethyl)-13-amino-2,5,8,11-tetraoxa-tetradecanamide (compound 76) as a colorless oil. IR (film) 3360, 1665, 1603, 1520, 1343, 1110 cm⁻¹; NMR δ 2.83 (t, 2H) 2.97 (t, 2H), 3.48 (t, 2H), 3.55-3.73 (m, 12H), 3.96 (s, 2H), 7.38-8.17 (AA'BB', 4H) ppm. Analysis calculated for $C_{18}H_{29}N_3O_7$: C, 54.07; H, 7.32; N, 10.51; found: C, 53.81; H, 7.32; N, 9.87.

b. Scheme 2 Reactions

Scheme 2 reactions are diagrammed as follows and described in detail below.

Scheme 2

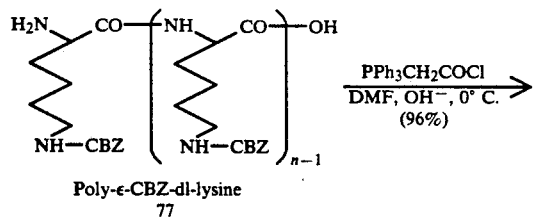

Poly-ε-CBZ-dl-lysine
77

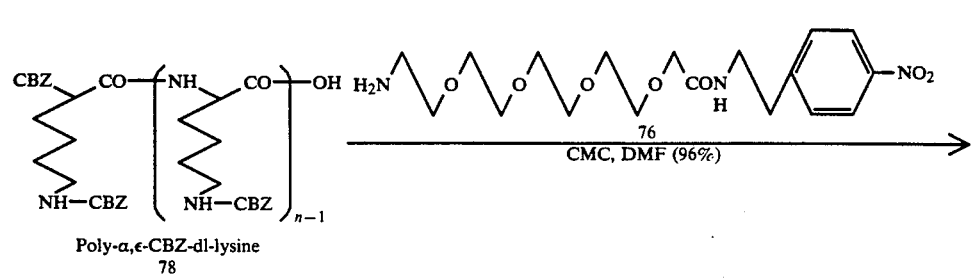

Poly-α,ε-CBZ-dl-lysine
78

-continued
Scheme 2

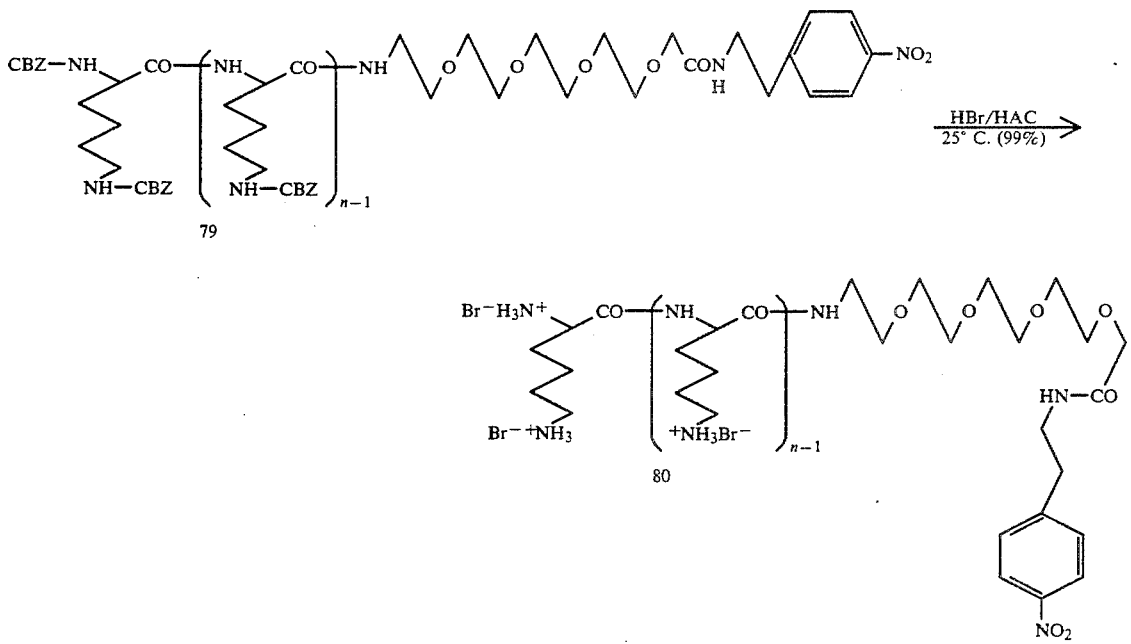

CBZ = carbobenzoxy; n = 65-74
CMC = 1-cyclohexyl-3-(2-morpholinoethyl)carbodiimide metho-p-toluenesulfonate

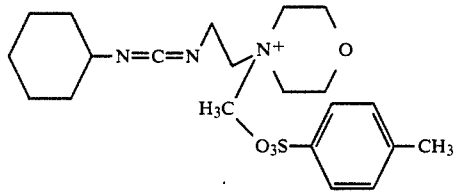

To a solution of poly-ε-CBZ-dl-lysine (compound 77) (100.0 mg, ~0.005 mmol) in 1.5 mL DMF was added 4N aqueous NaOH dropwise to adjust the pH to 9-10. Carbobenzoxy chloride (177.5 mg, 1.04 mmol, Aldrich) was slowly added dropwise at 0° C. over 30 min with stirring. During this addition the pH was maintained by the addition of 4N aqueous NaOH. The reaction mixture was then stirred at 25° C. until it gave a negative reaction to the Ninhydrin reagent (about 12 h), then acidified with 6N HCl to pH 2-3, stirred at 25° C. for 6 h and diluted with 10 mL doubly distilled water. The resulting precipitate was collected by centrifugation, washed twelve times with 5 mL doubly distilled water until no Cl was detected by aqueous $AgNO_3$, then washed twice with 5 mL acetone. The product was dried at 25° C. at 0.1 mm Hg absolute pressure for 12 h giving 96.7 mg (~96% yield) of poly-α,ε-CBZ-dl-lysine (compound 78) as a white powder. IR (KBr) 3304, 1698, 1654, 1625, 1533, 1453, 1400, 1255, 1136, 1022, 737, 700 $cm^{-1}$; NMR (DMF-$d_7$-CDCl$_3$) δ 1.37 (br, s), 1.78 (br, s), 2.36 (br, s), 3.01 (br, s), 4.90 (br, s), 7.15 (br, s) ppm.

To a solution of poly-α,ε-CBZ-dl-lysine 78 (20.0 mg, ~0.001 mmol) in DMF (3.0 mL) was added 1-cyclohexyl-3-(2-morpholinoethyl)carbodiimide metho-p-toluenesulfonate (CMC) (5.0 mg, 0.012 mmol). After stirring 20 min under $N_2$ at 0° C., the amino compound 76 (47.0 mg, 0.117 mmol) was added. The resulting mixture was stirred under $N_2$ at 25° C. for 72 h, then precipitated with 10 mL $H_2O$. The precipitate was collected by centrifugation, washed five times with 5 mL $H_2O$, three times with 5 mL acetone, then dried at 25° C. at 0.1 mm Hg absolute pressure for 12 h giving 19.2 mg (96% yield) of the coupling compound 79 as a pale powder. IR (KBr) 3304, 1699, 1659, 1627, 1453, 1404, 1252, 1137, 1024, 735, 696 $cm^{-1}$; NMR (DMF-$d_7$-CDCl$_3$) δ 1.37 (br s), 1.79 (br s), 2.43 (br s), 2.57 (br s), 3.00 (br s), 3.50-3.60 (m), 4.88 (br s), 7.12 (br s) ppm.

The coupling compound 79 (13.5 mg, ~0.4 μmol) was treated with 1.0 mL of a saturated solution of HBr in dry acetic acid in a small reaction flask equipped with a drying tube at 25° C. After stirring 40 min, the product was precipitated by addition of 10 mL dry ether. The precipitate was collected by centrifugation, washed eight times with 3 mL dry ether, and dried in a desiccator over concentrated $H_2SO$. and solid NaOH at 25° C. and 0.1 mm Hg absolute pressure for 24 h giving 10.0 mg (99% yield) of the hydrobromide 80 as a pale powder. IR (KBr) 3430, 1652, 1532, 1398 $cm^{-1}$; NMR ($D_2O$) δ 1.43 (br s, ~132H), 1.69-1.79 (m, ~265H), 3.00 (br s, ~131H), 3.57-3.67 (m, ~16H), 4.32 (br s, ~50H), 7.45-8.19 (AA'BB', ~4H).

C. Scheme 3 Reactions

Scheme 3 reactions are diagrammed as follows and described in detail below.

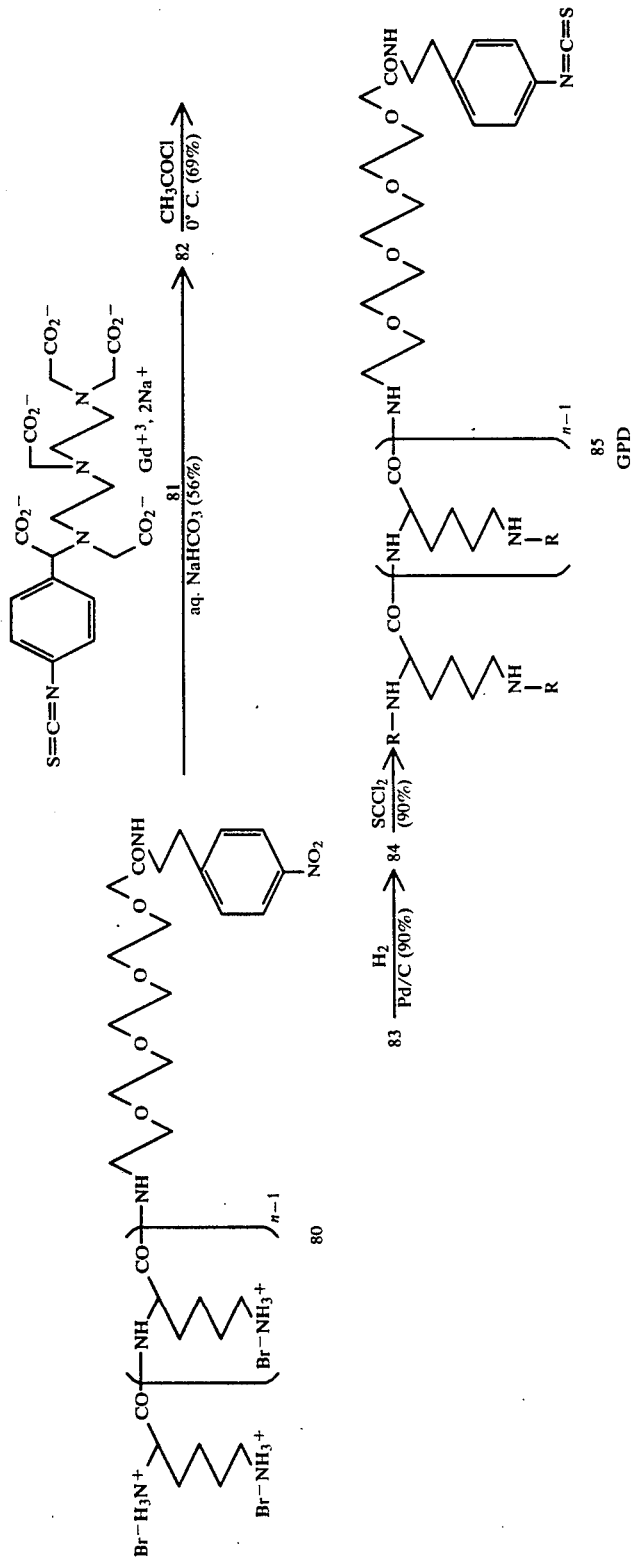

Aqueous 0.1N NaHCO₃ (0.35 mL) was added to a solution of the derivatized polylysine hydrobromide 80 (5.8 mg, ~0.42 μmol) in 0.5 mL H₂O to adjust the pH to 8-9. To the resulting suspension was added gadolinium (III)-3-(p-isothiocyanatobenzyl)diethyltriamine pentacetic acid [2Na⁺] (compound 81) (32.6 mg, 37 μmol). After stirring 48 h under N₂ at 25° C., the reaction mixture, which gave a positive reaction to Ninhydrin reagent, was transferred into a cellulose membrane tubing and exhaustively dialyzed against distilled water. The contents of the dialysis bag were lyophilized, giving 11.5 mg (~56% yield) of compound 82 as a yellowish powder. IR (KBr) 3427, 3148, 1622, 1402, 1097 cm⁻¹.

To effect acetylization, compound 82 (28.0 mg) was dissolved in 200 μL H₂O and the pH was adjusted to 8-9 with aqueous 4 N NaOH. This basic solution was cooled to 0° C. and acetyl chloride (200 μL, 2.8 μmol) was added slowly dropwise over 20 min with vigorous stirring. During this time the pH was maintained by the addition of 4N NaOH. The reaction mixture was then stirred at 25° C. for 2 h. At the end of this time the mixture gave a negative reaction with Ninhydrin reagent. After dialyzing against distilled water and lyophilizing, 19.4 mg (~96% yield) of compound 83 was obtained as a yellowish powder. IR (KBr) 3430, 3177, 1609, 1398, 1097 cm⁻¹.

In order to hydrogenate compound 83, the compound (19.0 mg) was dissolved in 2.0 mL H₂O in a Parr shaker bottle and 12.0 mg of 30% Pd/C was added. The suspension was shaken under H₂ at 40 psi pressure for 20 h. The catalyst was separated by centrifugation and washed twice with 2 mL H₂O. The water solution, which gave a positive reaction with Ninhydrin reagent, was concentrated and the product was precipitated by the addition of 5 mL acetone. The precipitate was collected by centrifugation and dried at 25° C. and 0.1 mm Hg absolute pressure for 12 h giving 16.8 mg (~90% yield) of compound 84 as a yellowish powder. IR (KBr) 3430, 3198, 1610, 1406, 1091 cm⁻¹.

For the final isothiocyanation reaction, a 0.2N solution of thiophosgene (12 mg) in 0.5 mL CHCl₃ was added slowly dropwise to a 2.0 mL solution of the amino compound 82 (16.5 mg) in saturated aqueous NaHCO₃ over 25 min at 25° C. with vigorous stirring. The resulting suspension was stirred at 25° C. for 2 h, then concentrated to dryness. The resulting solid was dissolved in 1.0 ml H₂O, dialyzed against distilled water, then lyophilized, giving 14.8 mg (~90% yield) of gadolinium chelate of polylysine derivative isothiocyanate (GPD, compound 85) as a yellowish powder. IR (KBr) 3423, 3205, 2108, 1602, 1400, 1096 cm⁻¹.

Having illustrated and described the principles of the present invention with reference to specific embodiments, it should be apparent to those persons skilled in the art that such invention may be modified in arrangement and detail without departing from such principles. For example, virtually any diagnostically or therapeutically active group can be covalently bonded to the terminal amines on the amplifier molecules of the present invention. Such bonding can be effected by any of a number of well-known acylation or alkylation reactions. By way of example, acid chlorides react with amines to yield amides, where the chloride is replaced by the amine group. Bonding to the amplifier can also be of pharmacologically active groups with hydrolyzable bonds. In the latter instance, a targeting amplified molecule would concentrate the desired pharmacologically active groups at the intended site in the body, whereupon hydrolysate enzymes present at the site would detach the active groups from the amplifier to permit easier circulation and diffusion of the active groups as separate molecules in the tissues at the site.

I claim:

1. A compound of the formula:

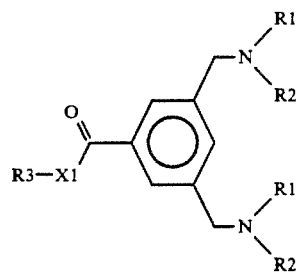

wherein:

R1 and R2 are independently selected from a group consisting of hydrogen, nitroxides, and paramagnetic metal ion chelates, the chelates selected from a group consisting of Gd(III), Mn(II), Mn(III), Fe(III), Cr(III), Cu(II), Co(II), Ni(II), Dy(III), Tb(III), and Nd(III) chelates;

X1 is selected from a group consisting of O and N; and

R3 is selected from a group consisting of lower (C₁-C₁₂) alkyls, C₄-C₁₂ hydrocarbon conjugated dienes, and maleimides.

2. A compound according to claim 1 wherein R3 is an N-substituted phenyl maleimide.

3. A composition of matter comprising the compound of claim 1 in a biocompatible, pharmacologically acceptable carrier.

4. The compound of claim 1 wherein:

R1 and R2 are nitroxides of the formula

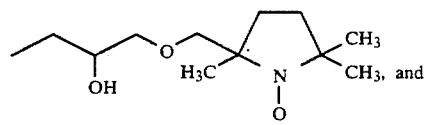

R3 has the formula

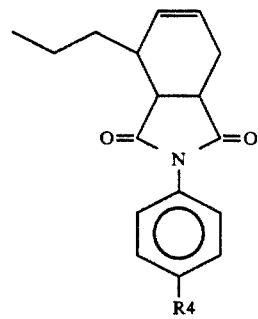

wherein R4 is selected from the group consisting of amino, nitro, azido, and isothiocyanate moieties.

5. The compound of claim 1 wherein:
each R1 is H;
each R2 is a chelate of the formula:

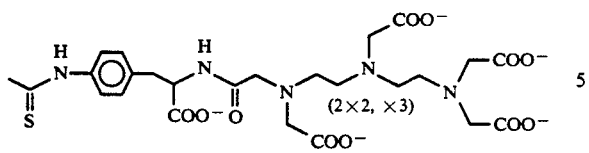

wherein X2 is a monovalent alkali metal cation and X3 is a trivalent paramagnetic metal cation selected from a group consisting of Gd(III), Mn(III), Fe(III), Cr(III), Dy(III), Tb(III), and Nd(III); and R3 has the formula

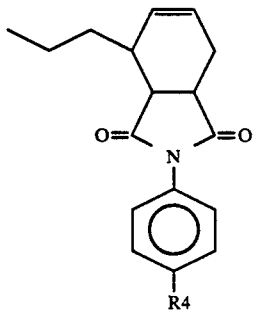

wherein R4 is selected from a group consisting of amino, nitro, azido, and isothiocyanate moieties.

6. The compound of claim 5 wherein X2 is Na+ and X3 is $Gd^{3+}$.

7. A compound according to claim 2 wherein R3 is an N-isocyanatophenyl maleimide.

8. A compound of the formula:

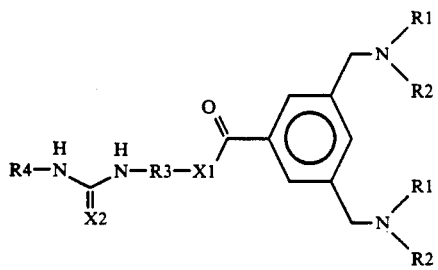

wherein
R1 and R2 are independently selected from a group consisting of H, nitroxides, and paramagnetic metal ion chelates, the chelates selected from a group consisting of Gd(III), Mn(II), Mn(III), Fe(III), Cr(III), Cu(II), Co(II), Ni(II), Dy(III), Tb(III), and Nd(III) chelates;
X1 is selected from a group consisting of O and N;
X2 is selected from a group consisting of O and S;
R3 is a maleimide; and
R4 is selected from a group consisting of polyamines, polylysines, polyethyleneimines, and liposomes possessing a multiplicity of exposed primary amines.

9. A compound that selectively attaches to a target in the body of a human or other warm-blooded animal, the compound of the formula:

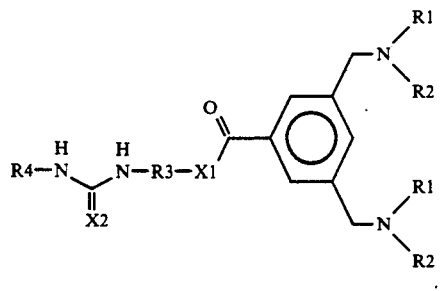

wherein
R1 and R2 are independently selected from a group consisting of hydrogen, nitroxides, and paramagnetic metal ion chelates, the chelates selected from a group consisting of Gd(III), Mn(II), Mn(III), Fe(III), Cr(III), Cu(II), Co(II), Ni(II), Dy(III), Tb(III), and Nd(III) chelates;
X1 is selected from a group consisting of O and N;
X2 is selected from a group consisting of O and S;
R3 is selected from a group consisting of lower ($C_1$-$C_{12}$) alkyls, $C_4$-$C_{12}$ hydrocarbon conjugated dienes, and maleimides; and
R4 is an immunoglobulin seroreactive with the target.

10. A compound according to claim 9 for MRI contrast enhancement, wherein:
each R1 is H and each R2 is a chelate of the formula

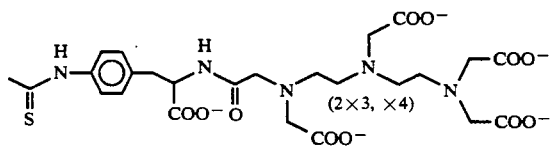

wherein X3 is a monovalent alkali metal cation and X4 is a trivalent paramagnetic metal ion selected from a group consisting of Gd(III), Mn(III), Fe(III), Cr(III), Dy(III), Tb(III), and Nd(III); and R3 is a maleimide of the formula

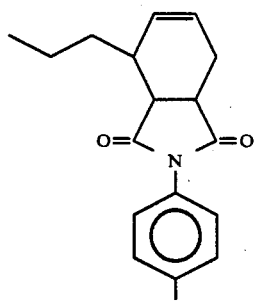

11. The compound of claim 8 wherein R4 has at least one exposed isothiocyanate moiety.

12. The compound of claim 8 wherein R4 is covalently bonded via a thiourea linkage to an immunoglobulin.

13. A composition of matter comprising the compound of claim 8 in a biocompatible, pharmacologically acceptable carrier.

14. A composition of matter comprising the compound of claim 9 in a biocompatible, pharmacologically acceptable carrier.

15. The compound of claim 10 wherein X3 is Na+ and X4 is $Gd^{3+}$.

16. A compound according to claim 9, wherein R1 and R2 are nitroxides.

* * * * *

UNITED STATES PATENT AND TRADEMARK OFFICE
CERTIFICATE OF CORRECTION

PATENT NO. : 5,135,737

DATED : August 4, 1992

INVENTOR(S) : John F. W. Keana

It is certified that error appears in the above-identified patent and that said Letters Patent is hereby corrected as shown below:

Column 1, line 60, "in vivo" should be --*in vivo*--;

Column 2, line 44, "in vivo" should be --*in vivo*--;

Column 3, line 2, "06/928,943 ,now" should be --06/928,943, now--;

Column 3, line 38, after "patient" insert --.--;

Column 5, line 26, "in vacuo" should be --*in vacuo*--;

Column 5, line 27, "2N HCl" should be --2 $\underline{N}$ HCl--;

Column 7, line 3, "2N HCl" should be --2 $\underline{N}$ HCl--;

Column 7, line 47, "in vacuo" should be --*in vacuo*--;

Column 8, line 63, "1N NaOH" should be --1 $\underline{N}$ NaOH--;

Column 8, line 64, "2N HCl" should be --2 $\underline{N}$ HCl--;

Column 9, line 7, "8.66" should be --8.66--;

Column 9, line 44, "1N HCl" should be --1 $\underline{N}$ HCl--;

Column 9, lines 45-46, "1N NaOH" should be --1 $\underline{N}$ NaOH--;

Column 10, line 50, "in vacuo" should be --*in vacuo*--;

Column 10, line 55, "(s, 4 ," should be --(s, 4),--;

Column 10, line 56, "m,(1)," should be --(m, 1),--;

UNITED STATES PATENT AND TRADEMARK OFFICE
CERTIFICATE OF CORRECTION

PATENT NO. : 5,135,737

DATED : August 4, 1992

INVENTOR(S) : John F. W. Keana

Page 2 of 7

It is certified that error appears in the above-identified patent and that said Letters Patent is hereby corrected as shown below:

Column 10, line 58, "-with" should be --with--;

Column 11, line 28, after "1535" insert --,--;

Column 12, line 10, "I." should be --I,--;

Column 12, line 20, "$a_n x$" should be --$a_N$--;

Column 12, line 42, "6(2" should be --6-(2--;

Column 12, lines 49-50 (specification page 23, line 12), "$C_{169}H_{309}N_{19}O_{39}7\ H_2O$:" should be --$C_{169}H_{309}N_{19}O_{39} \cdot 7\ H_2O$:--;

Column 13, line 1, "R'" should be --R·--;

Column 14, line 41, "R'" should be --R·--;

Column 15, line 3, "75 mL" should be --75 µL--;

Column 15, line 4, "0.2N, 15 µmol)" should be --(0.2 N, 15 µmol)--;

Column 15, line 39, "R'" should be --R·--;

Column 15, line 50, "immunoglobulins-(antibodies)" should be --immunoglobulins (antibodies)--;

Column 17, line 51, "NMR 2.20" should be --NMR δ 2.20--;

Column 18, line 30, "Tert-butylamine" should be --<u>Tert</u>-butylamine--;

Column 18, line 51, "(s, 4)" should be --(s, 4),--;

UNITED STATES PATENT AND TRADEMARK OFFICE
CERTIFICATE OF CORRECTION

PATENT NO. : 5,135,737

DATED : August 4, 1992

INVENTOR(S) : John F. W. Keana

It is certified that error appears in the above-identified patent and that said Letters Patent is hereby corrected as shown below:

Column 18, line 62, delete the comma after "target";

Column 19, line 31, "Audio" should be --Azido--;

Column 19, line 47, "--C NMR" should be --$^{13}$C NMR--;

Column 19, line 58, "Epoxyazide 2B" should be --Epoxyazide 28--;

Column 20, line 59, "6 44" should be --6.44--;

Column 21, line 5, "$K_l$ = 22" should be --$K_a$ = 22--;

Column 21, line 24, "NaHCO:," should be --$NaHCO_3$,--;

Column 22, line 17, "1N" should be --1 $\underline{N}$--;

Column 22, line 20, "$NaHCO^3$" should be --$NaHCO_3$--;

Column 22, lines 44-45, "in vacuo" should be --<u>in vacuo</u>--;

Column 23, line 16, "m/e" should be --<u>m</u>/<u>e</u>--;

Column 23, line 34, "1N" should be --1 $\underline{N}$--;

Column 23, line 36, "5° C" should be --25° C--;

Column 23, line 37, "1N" should be --1 $\underline{N}$--;

Column 23, line 64, "1N" should be --1 $\underline{N}$--;

Column 24, line 21, "1N" should be --1 $\underline{N}$--;

UNITED STATES PATENT AND TRADEMARK OFFICE
CERTIFICATE OF CORRECTION

PATENT NO. : 5,135,737

DATED : August 4, 1992

INVENTOR(S) : John F. W. Keana

It is certified that error appears in the above-identified patent and that said Letters Patent is hereby corrected as shown below:

Column 25, lines 1-8, chemical drawing (39) should read:

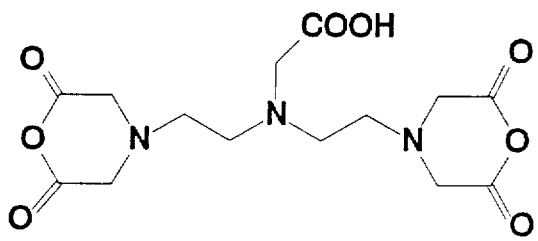

Column 26, line 7, "M" should be --$\underline{M}$--;

Column 27, line 7, "supra" should be --<u>supra</u>--;

Column 27, line 47, "cm$^{-1}$:" should be --cm$^{-1}$.--;

Column 29, line 1, "0.2N" should be --0.2 $\underline{N}$--;

Column 30, line 18, "1N HCl" should be --1 $\underline{N}$ HCl--;

Column 31, line 63, "(dec):" should be --(dec);--;

Column 31, line 64, "5 02" should be --5.02--;

Column 32, lines 47-48, "triphenylphosphoniu-m-salt" should be --triphenylphosphonium salt--;

Column 33, line 16, "$C_{37}H_{32}BrN_2O_4PS.H_2O$" should be --$C_{37}H_{32}BrN_2O_4PS \cdot H_2O$--;

UNITED STATES PATENT AND TRADEMARK OFFICE
CERTIFICATE OF CORRECTION

PATENT NO. : 5,135,737

DATED : August 4, 1992

INVENTOR(S) : John F. W. Keana

It is certified that error appears in the above-identified patent and that said Letters Patent is hereby corrected as shown below:

Column 33, line 30, "0 0278" should be --0.0278--;

Column 33, line 40, "$C_{67}H_{83}BrN_8O_{10}PS.3H_2O$" should be --$C_{67}H_{83}BrN_8O_{10}PS \cdot 3H_2O$--;

Column 34, line 8, "supra" should be --_supra_--;

Column 35, line 46, "40°--45° C" should be --40-45°C--;

Column 36, line 29, "6.70:" should be --6.70;--;

Column 37, line 37, "2 N HCl" should be --2 _N_ HCl--;

Column 38, line 29, "2.5M" should be --2.5 _M_--;

Column 39, line 25, "$C_{26}H_{39}N_3.5H_2O$" should be --$C_{26}H_{39}N_3 \cdot 1.5H_2O$--;

Column 39, line 42, after "was" and before "to" add --added slowly via syringe--;

Column 39, line 44, "ice/$H_2$/O" should be --ice/$H_2O$--;

Column 39, line 45, "7N" should be --7 _N_--;

Column 40, line 51 "(m,2," should be --(m,2),--;

Column 40, line 68 "0.12N" should be --0.12 _N_--;

Column 42, lines 14-15 "$C_{22}H_{23}N_4O_{10}S_1Gd_1Na_28.5H_2O$:" should be --$C_{22}H_{23}N_4O_{10}S_1Gd_1Na_2 \cdot 8.5H_2O$:--;

UNITED STATES PATENT AND TRADEMARK OFFICE
CERTIFICATE OF CORRECTION

PATENT NO. : 5,135,737

DATED : August 4, 1992

INVENTOR(S) : John F. W. Keana

It is certified that error appears in the above-identified patent and that said Letters Patent is hereby corrected as shown below:

Column 43, line 50 "6N"
should be --6 N--;

Column 45, lines 6-7,
"1 azido-11-tetrahydropyranyloxy-3,6,9-trioxaundecane"
should be --1-azido-11-tetrahydropyranyloxy-3,6,9-trioxaundecane--;

Column 45, line 7, "Oil" should be --oil--;

Column 46, line 24, "1N" should be --1 N--;

Column 46, line 26, "4N" should be --4 N--;

Column 47, line 41, "4N" should be --4 N--;

Column 47, line 45, "4N" should be --4 N--;

Column 47, line 48, "6N" should be --6 N--;

Column 47, line 52, "Cl" should be --Cl$^-$--;

Column 48, line 56, "H$_2$SO." should be --H$_2$SO$_4$--;

Column 51, line 1, "1N" should be --1 N--;

Column 51, line 17, "4 N" should be --4 N--;

Column 51, line 21, "4N" should be --4 N--.

UNITED STATES PATENT AND TRADEMARK OFFICE
CERTIFICATE OF CORRECTION

PATENT NO. : 5,135,737
DATED : August 4, 1992
INVENTOR(S) : John F. W. Keana

It is certified that error appears in the above-indentified patent and that said Letters Patent is hereby corrected as shown below:

Col. 51, line 41, "0.2N" should be --0.2 N--.

Signed and Sealed this

Fifth Day of July, 1994

Attest:

BRUCE LEHMAN

Attesting Officer

Commissioner of Patents and Trademarks